US008784293B2

(12) United States Patent
Berka et al.

(10) Patent No.: US 8,784,293 B2
(45) Date of Patent: Jul. 22, 2014

(54) SYSTEMS AND METHODS FOR OPTIMIZATION OF SLEEP AND POST-SLEEP PERFORMANCE

(71) Applicant: Advanced Brain Monitoring, Inc., Carlsbad, CA (US)

(72) Inventors: Christine Berka, Carlsbad, CA (US); Djordje Popovic, Carlsbad, CA (US); Dan Levendowski, Carlsbad, CA (US); Gene Davis, Carlsbad, CA (US); Catherine McConnell, Carlsbad, CA (US); Matthew A. Yanagi, Carlsbad, CA (US)

(73) Assignee: Advanced Brain Monitoring, Inc., Carlsbad, CA (US)

( * ) Notice: Subject to any disclaimer, the term of this patent is extended or adjusted under 35 U.S.C. 154(b) by 0 days.

(21) Appl. No.: 13/910,709

(22) Filed: Jun. 5, 2013

(65) Prior Publication Data

US 2013/0303837 A1    Nov. 14, 2013

Related U.S. Application Data

(63) Continuation-in-part of application No. 12/574,631, filed on Oct. 6, 2009, now Pat. No. 8,628,462.

(60) Provisional application No. 61/656,844, filed on Jun. 7, 2012, provisional application No. 61/656,958, filed on Jun. 7, 2012, provisional application No. 61/103,512, filed on Oct. 7, 2008.

(51) Int. Cl.
  *A61M 21/00* (2006.01)
  *A61M 21/02* (2006.01)

(52) U.S. Cl.
  CPC ............... *A61M 21/00* (2013.01); *A61M 21/02* (2013.01); *A61M 2021/0027* (2013.01); *A61M 230/10* (2013.01); *A61M 2230/50* (2013.01)
  USPC ............................................. 600/26; 600/27

(58) Field of Classification Search
  CPC ................ A61M 21/02; A61M 21/00; A61M 2021/0044; A61M 2021/0027; A61M 2021/0066; A61M 2021/0083; A61M 2230/10; A61M 2230/50; A61M 2205/3368; A61M 2205/8206; A61M 2205/507
  USPC ...................................................... 600/27, 26
  See application file for complete search history.

(56) References Cited

U.S. PATENT DOCUMENTS 5,474,082 A * 12/1995 Junker .......................... 600/545
5,507,716 A *  4/1996 LaBerge et al. ................. 600/27

(Continued)

OTHER PUBLICATIONS

International Search Report and Written Opinion for PCT/US2009/059836 issued May 13, 2010.

*Primary Examiner* — Christine Matthews
*Assistant Examiner* — Sunita Reddy
(74) *Attorney, Agent, or Firm* — Procopio Cory Hargreaves & Savitch LLP

(57) ABSTRACT

Systems and methods for optimizing sleep and post-sleep performance. In an embodiment, a system comprising a device and sleep mask are provided. The mask may comprise electroencephalographic (EEG) sensors and one or more stimulation elements configured to stimulate the senses of a wearer of the mask. The mask may be releasably and electrically coupled to a device which receives EEG signals from the mask, determines current and target sleep states based, at least in part, on the EEG signals, and uses this determination to tailor a sleep architecture of the wearer by controlling the stimulation elements. The mask may be a soft mask which utilizes conductive thread embroidered into one or more textile layers. In an embodiment, the stimulation elements may comprise one or more heating elements, electroluminescent panels, and speakers. In addition, the EEG sensors may comprise hybrid sensors comprising hydrogel in a conductive spacer fabric.

23 Claims, 13 Drawing Sheets

(56) References Cited

U.S. PATENT DOCUMENTS

| | | | |
|---|---|---|---|
| 5,692,517 A * | 12/1997 | Junker | 600/545 |
| 6,416,471 B1 * | 7/2002 | Kumar et al. | 600/300 |
| 6,454,708 B1 * | 9/2002 | Ferguson et al. | 600/300 |
| 7,041,049 B1 * | 5/2006 | Raniere | 600/26 |
| 8,069,852 B2 | 12/2011 | Burton et al. | |
| 8,355,769 B2 | 1/2013 | Levendowski et al. | |
| 2002/0169384 A1 | 11/2002 | Kowallik et al. | |
| 2004/0002742 A1 | 1/2004 | Florio | |
| 2005/0085738 A1 | 4/2005 | Stahmann et al. | |
| 2005/0143617 A1 | 6/2005 | Auphan | |
| 2005/0283039 A1 | 12/2005 | Cornel | |
| 2006/0106275 A1 | 5/2006 | Raniere | |
| 2006/0241708 A1 | 10/2006 | Boute | |
| 2007/0249952 A1 | 10/2007 | Rubin et al. | |
| 2008/0234785 A1 | 9/2008 | Nakayama et al. | |
| 2009/0030489 A1 * | 1/2009 | Asvadi et al. | 607/88 |
| 2009/0207028 A1 | 8/2009 | Kubey et al. | |
| 2012/0161783 A1 | 6/2012 | Berka et al. | |

* cited by examiner

SYSTEMS AND METHODS FOR OPTIMIZATION OF SLEEP AND POST-SLEEP PERFORMANCE

PRIORITY

This application claims the benefit of U.S. Provisional Patent App. No. 61/656,844, entitled "Systems and Methods for Optimization of Sleep and Post-Sleep" and filed on Jun. 7, 2012, and U.S. Provisional Patent App. No. 61/656,958, entitled "Systems and Methods for Optimization of Sleep and Post-Sleep" and filed on Jun. 7, 2012, and is a continuation-in-part of U.S. patent application Ser. No. 12/574,631, entitled "Systems and Methods for Optimization of Sleep and Post-Sleep Performance," filed on Oct. 6, 2009, published as U.S. Patent Pub. No. 2010/0087701 on Apr. 8, 2010, and issued as U.S. Pat. No. 8,628,462 on Jan. 14, 2014, which in turn claims the benefit of U.S. Provisional Patent App. No. 61/103,512, entitled "Apparatus and Method for Optimization of Sleep and Post-Sleep Performance" and filed Oct. 7, 2008, all of which are hereby incorporated herein by reference in their entireties as if set forth in full.

GOVERNMENT LICENSE RIGHTS

This invention was made with government support under Contract No. W3194Q-09-C-0281, awarded by the Defense Advanced Research Projects Agency and the Small Business Innovation Research program. The government has certain rights in the invention.

FIELD OF THE INVENTION

The present invention relates generally to the field of monitoring and improving sleep architecture and more specifically to systems and methods for optimizing the sleep architecture of a subject using a wearable device.

BACKGROUND

On average, healthy adults sleep between six and nine hours per night. The exact amount of sleep required by a person may vary due to a number of factors associated with the person, such as the age of the person, the level of physical activity of the person, the use of alcohol, drugs, and/or medications by the person, and the overall condition of health. Contemporary sleep science distinguishes five stages of sleep (including wakefulness as a pre-sleep stage): a rested wakeful stage, non-rapid eye movement (NREM) sleep stages 1, 2, and 3, and a rapid eye movement (REM) stage. The various stages of sleep may be identified using various techniques, such as monitoring brainwave patterns using an electroencephalogram (EEG) technique, monitoring eye movements using a electrooculogram (EOG) technique, monitoring the movements of the chin using electromyogram (EMG) techniques, and/or other techniques for monitoring the physiological characteristics of a subject.

Rested wakefulness is characterized by low amplitude alpha waves (8-12 Hz) present in an EEG of a subject whose brain waves are being monitored. Alpha waves are brain waves typically exhibited while a subject is in a wakeful and relaxed state with the subject's eyes being closed. The alpha waves typically decrease in amplitude while the subject's eyes are opened or the subject is in a drowsy or sleeping state.

NREM Stage 1 is characterized by irregular theta waves of low amplitude present in the EEG of a subject being monitored and slow rolling eye movements present in an EOG of the subject. NREM Stage 2 is characterized by high frequency (12-16 Hz) bursts of brain activity called sleep spindles riding on top of slower brain waves of higher amplitude. During the NREM Stage 2, a gradual decline in heart rate, respiration, and core body temperature occurs as the body prepares to enter deep sleep. NREM Stage 3 is characterized by delta waves (1-3 Hz) of large amplitude that dominate for more than 20% of the time. Rapid eye movement (REM) sleep presents with a marked drop in muscle tone and bursts of rapid eye movements that can be seen in the EOG. The EEG in REM is not specific and resembles that of wakefulness or NREM Stage 1 sleep. Other physiological signals (e.g., breathing, heart rate) during REM sleep also exhibit a pattern similar to that occurring in an awakened individual.

Sleep stages come in cycles that repeat on average four to six times a night, with each cycle lasting approximately ninety to one-hundred-and-twenty minutes. FIG. 1 illustrates a typical sleep cycle that includes an NREM Stage 1, followed by an NREM Stage 2, followed by an NREM Stage 3, which is followed by a REM stage. The order of the stages of a sleep cycle and the length of the sleep stages may vary from person to person and from sleep cycle to sleep cycle. For example, NREM Stage 3 may be more prevalent during sleep cycles that occur early in the night, while NREM Stage 2 and REM sleep stages may be more prevalent in sleep cycles that occur later in the night. The sequence and/or length of sleep stages (NREM sleep stages 1, 2, 3 or the REM sleep stage) during an (overnight) sleep or (daytime) nap, sometimes interrupted with brief periods of wakefulness, is referred to as sleep architecture.

For optimal results from sleep, a balance between sleep stages is typically required over longer periods of time, such as days or weeks. Sleep deprivation—i.e., the persistent lack of a particular sleep stage (usually REM or NREM Stage 3)—over a period of even a few days can result in the deterioration of cognitive performance of a subject, even if the subject has taken long naps and the total amount of sleep time over the course of each day is relatively normal. For example, a person requiring eight hours of sleep may have only slept six hours each night over a three day period, but may have taken a two hour nap each day. The total number of hours of sleep for each day equals the eight hours required by the person. However, the person may not have experienced sufficient time in one or more particular sleep stages, thereby causing sleep deprivation in the person. Sleep deprivation can affect cognitive performance as well as the physical dexterity of the subject. In addition, the point in a sleep cycle which the subject has experienced just prior to waking can crucially affect the post-sleep dexterity, cognitive performance, and subjective feeling of the subject. For example, a sleeper wakened from late NREM stages 2 or 3 often experiences significant sleep inertia, such as a feeling of grogginess that may persist for up to thirty minutes or an hour after waking.

A large number of people have difficulties with falling asleep, maintaining sleep, experience frequent awakenings, or just do not use their sleep time as well as they could. The effects of even small amounts of sleep loss accumulate over time resulting in a "sleep debt" which manifests itself in the form of increasing impairment of alertness, memory, and decision-making. Vigilance, memory, decision-making, and other neurocognitive processes are all impacted by poor sleep quality, sleep deprivation, and accumulating sleep debt with potentially detrimental consequences. For example, recent National Aeronautics and Space Administration (NASA) technical reports reveal that pilots often experience brief episodes of unintentional sleep while flying. In the general population, chronic sleep loss is increasingly considered a serious public health and safety concern, and impaired vigilance is shown to be a primary contributor to transportation and industrial accidents.

As a practical example, sleep deprivation is particularly problematic among active servicemen. Military operations often combine high-performance demands and significant physical efforts with irregular sleep schedules. Small amounts of sleep loss accumulate over time, resulting in a sleep debt for these individuals. This sleep debt may manifest itself as impairments of cognitive functions and manual dexterity with potentially detrimental consequences in military, as well as civilian, settings.

Many people do not realize they are not sleeping well and are, nonetheless, suffering the consequences of inefficient sleep. Other people attempt to overcome sleep-related problems by taking sleep-inducing or sleep-assisting drugs, such as pharmacological stimulants (e.g., caffeine), attending psychological therapy, using relaxation techniques prior to sleeping, and the like. However, while temporary amelioration of the effects of sleep deprivation can be achieved using some of these techniques, an adequate amount of sleep that is commensurate with a person's accumulated sleep debt is indispensable for complete recuperation in the long run.

Many situations (e.g., in a military context) do not allow for a regular bout of nocturnal sleep. In such situations, brief naps, taken at various times throughout the day, have been advocated as an effective and natural means of countering fatigue and improving performance. Unfortunately, it is not easy to device an optimal schedule for napping, because the effects of a nap on dexterity and cognition depend, not only upon its duration, but also upon the sleep quality, point on the circadian cycle at which the nap occurred, and depth of sleep from which the subject is awakened.

The sleep architecture of a nap is especially important, because various stages of sleep contribute differently to recuperation. Naps composed only of light sleep (NREM Stage 1) do no not improve performance, whereas even a few minutes of solid sleep (NREM Stage 2) boost alertness, attention, and motor performance. Deep sleep (NREM Stage 3) is desirable because of its effects on stress reduction and skill acquisition. However, paradoxically, interruptions of a nap during NREM Stage 3 sleep (e.g., due to an alarm) may lead to decrements in performance as a result of sleep inertia. Adequate balance among the sleep stages over longer periods of time is also important. A persistent lack of, for example, REM sleep, can result in a decline in performance, even if the total sleep time per day appears adequate. Thus, simplified paradigms that only prescribe durations and frequencies for napping will not result in a consistent and effective mitigation of performance deficits.

SUMMARY

Systems and methods for optimizing the sleep performance of a subject person are disclosed. The systems and methods can be used to optimize the sleep and post-sleep performance of individuals regardless of their environment and the time available for sleep. The systems and method may be used in domiciliary settings, such as in a subject's home and/or in operational settings, such as a hospital, sleep clinic, or a field deployment for industry or military. The systems and methods may account for factors that determine the effects of a sleep episode on dexterity, cognitive functions, and the subjective feeling of fatigue after sleeping, including duration and sleep architecture of the sleep episode, point on the circadian cycle at which the episode occurred, the amount of sleep debt accumulated prior to the episode, and the subject's susceptibility to sleep deprivation. Embodiments of the systems and methods for obtaining efficient sleep periods may also include monitoring of sleep architecture over a longer period of time (e.g., a couple of days, or a few weeks), measurement of accumulated sleep debt, assessment and/or tailoring of the sleep architecture for each subsequent sleep episode, determining a desired sleep state in which the subject should be, and generating sensory stimuli for guiding the subject to the desired sleep state.

According to an embodiment, a method for optimizing the sleep of a subject is provided. The method includes monitoring at least one physiological characteristic of a subject indicative of a sleep state, and determining a current sleep state of the subject from the at least one monitored physiological characteristic. The method further includes determining a desired sleep state for the subject, and generating at least one sensory stimulus to guide the subject toward the desired sleep state if the current sleep state differs from the current sleep state.

According to another embodiment, an apparatus for optimizing sleep of a subject is provided. The apparatus includes a physiological characteristics monitor configured to monitor at least one physiological characteristic of a subject indicative of a sleep state of the subject and to generate physiological data representing the physiological characteristics of the subject. The apparatus also includes a data processor for processing the physiological data. The data processor may include a sleep staging component and a rules engine. The sleep staging component may be configured to determine a current sleep state of the sleeper using the physiological data. The rules engine may be configured to determine a desired sleep state for the subject and determine one more stimuli to guide the subject to the desired sleep state from the current sleep state. The apparatus may also include a stimulus generator configured to generate one or more stimuli to guide the subject toward the desired sleep state.

According to yet another embodiment, a computer-readable medium comprising processor-executable instructions that, when executed, direct a computer system to perform actions is provided. The computer-readable medium includes instructions for monitoring at least one physiological characteristic of a subject indicative of a sleep state, determining a current sleep state of the subject from the at least one monitored physiological characteristic, determining a desired sleep state for the subject, and generating at least one sensory stimulus to guide the subject toward the desired sleep state if the current sleep state differs from the current sleep state.

In another embodiment, a system for tailoring sleep architecture is disclosed. The system comprises: one or more coupling elements configured to electrically couple a device to a mask; the mask, wherein the mask is configured to be worn by a user, and wherein the mask comprises one or more electroencephalographic sensors, wherein each of the one or more electroencephalographic sensors comprises hydrogel in a conductive spacer fabric, a heater element configured to generate heat, wherein the heater element comprises insulated conductive thread electrically coupled to one or more of the one or more coupling elements, a visual element configured to generate light, wherein the visual element comprises one or more electroluminescent panels, and conductive thread electrically coupled to one or more of the one or more coupling elements, and an audio element configured to generate sound, wherein the audio element comprises one or more speakers, and conductive thread electrically coupled to one or more of the one or more coupling elements; and the device, wherein the device comprises a controller comprising one or more modules that, when the device is electrically coupled to the mask, receive one or more electroencephalographic signals from the one or more electroencephalographic sensors, determine a current sleep state and a target sleep state based, at least in part, on the one or more electroencephalographic signals, and, if the current sleep state and the target sleep state are different, control one or more of the heater element, visual element, and audio element, via the one or more coupling elements, to guide the user to the target sleep state.

In an another embodiment, a mask configured to be worn by a user, wherein the mask comprises one or more electroencephalographic sensors, wherein each of the one or more electroencephalographic sensors is configured to acquire electrical activity from the user, and one or more stimulation elements, wherein each of the one or more stimulation elements is configured to provide one or more sensory stimuli to the user; and a device comprising a controller comprising one or more modules that, when the device is electrically coupled to the mask, receive one or more electroencephalographic signals from the one or more electroencephalographic sensors, determine a current sleep state and a target sleep state based, at least in part, on the one or more electroencephalographic signals, and, if the current sleep state and the target sleep state are different, control one or more of the one or more stimulation elements to guide the user to the target sleep state.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Embodiments of the present invention provide systems and method for optimization of sleep and post-sleep performance in operational and domiciliary settings by guiding a sleeper through an optimal sleep pattern with the goals of decreasing sleep latency, increasing sleep efficiency, ensuring balance among sleep states over longer periods of time and avoiding sleep inertia upon awakening. Embodiments of the present invention monitor physiological signals to identify a current sleep state being experienced by a sleeping subject, determine a desired sleep state that the subject should be experiencing based on sleep architecture data for the subject, identify sensory stimuli that may be applied to the subject to guide the subject to the desired sleep state from the current sleep state, and generate the sensory stimuli to guide the subject from the current sleep state to the desired sleep state. Continual monitoring of physiological signals of the sleeping subject allows the system to adapt to changes in the sleep state of the subject and to adjust the stimuli being generated. The sleeping subject may be guided through one or more intermediate sleep states in order to reach the desired sleep state. Embodiments also provide for detection and protection of the sleeping subject from environmental disturbances, such as noise, light, and temperature changes.

Embodiments also maintain a record of sleeping and napping episodes and the subject's sleep architecture over time (e.g., days, weeks, months, etc.). The cumulative sleeping and napping data can be used to develop a personalized sleep profile for the subject. The personalized sleep profile data can be used to generate a set of customized rules for determining an ideal sleep state for the subject based on the current sleep state of the subject and the parameters of the current sleep episode. The rules can be used to optimize a sleep episode and post-sleep performance. Post-sleep performance refers to the performance of a subject engaging in a task that requires use of motor and/or cognitive skills of the performer.

Embodiments of the present invention provide systems and methods for guiding the sleep of a subject to achieve efficient sleep periods of a subject even where there is little sleep time available, when the sleep periods are interrupted, or when the subject wishes to wake up at a particular time. The systems and method can be used to optimize the sleep cycles of a subject to allow the subject to experience more efficient sleep, to wake feeling more refreshed, to require less sleep than the subject may have required without the optimizations, and to reduce the impact of sleep inertia.

Process Overview

Figure 1:
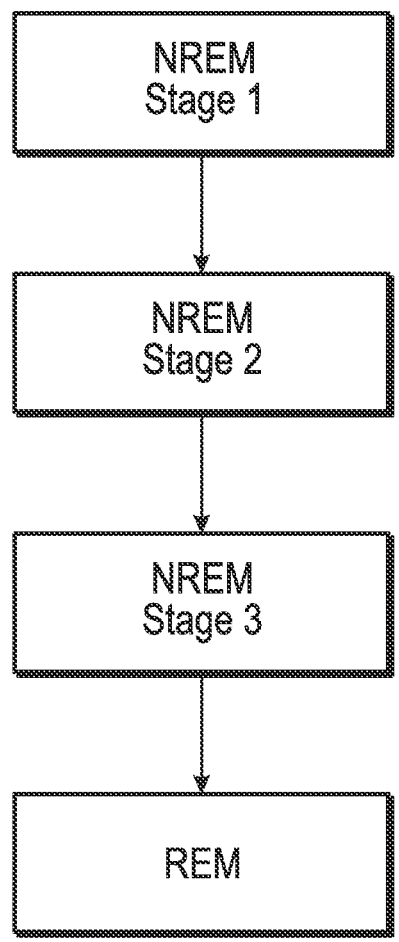
FIG. 1 illustrates a block diagram illustrating a typical sleep cycle.
Figure 2:
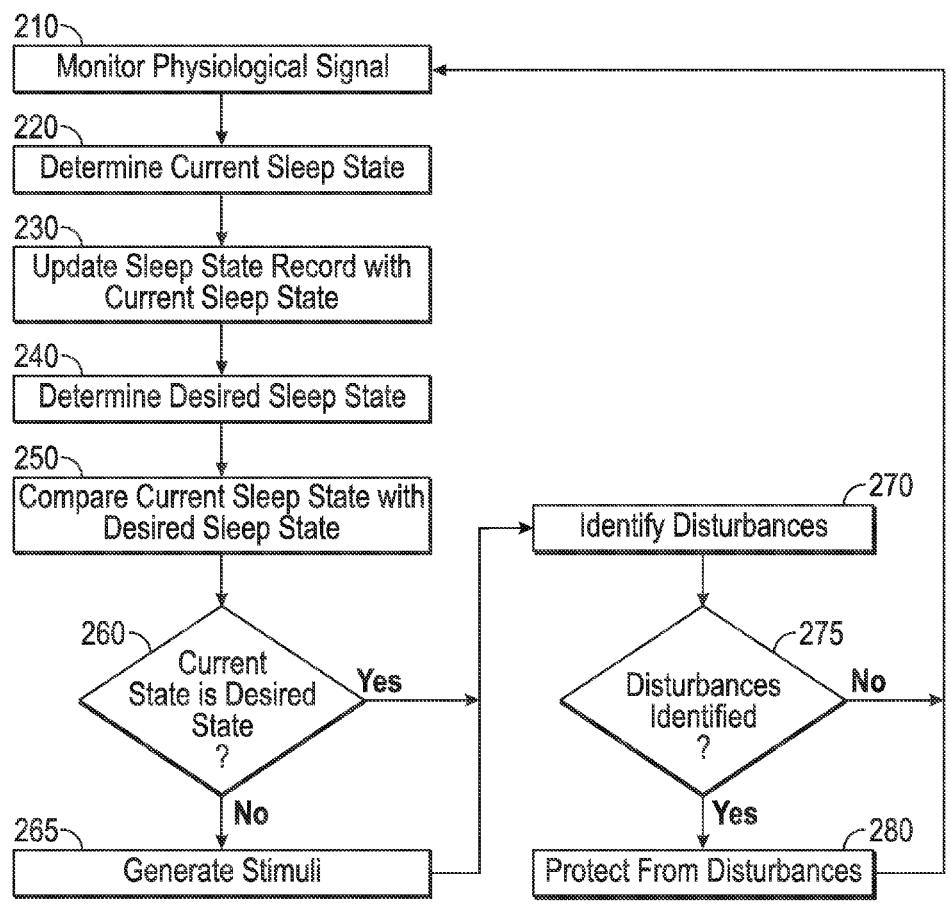
FIG. 2 illustrates a flow diagram of a method for optimizing the sleep of a subject by guiding the subject to desired sleep stages, according to an embodiment.

FIG. 2 is a flow diagram of a method for optimizing the sleep of a subject by guiding the subject through desired sleep stages, according to an embodiment. Embodiments of the system which implement the described methods are described afterwards. One or more physiological signals, indicative of a sleep state of a sleeping subject, are monitored (step 210). According to an embodiment, the physiological signals can include, but are not limited to, electroencephalogram (EEG), electrooculogram (EOG), electromyogram (EMG), respiration, heart rate, body movement, galvanic skin reaction, blood pressure, blood flow, blood chemistry, behavioral responses, or some combination thereof. In general, the signals are selected so as to provide information sufficient to identify sleep states and changes between them. Appropriate sensors and equipment for monitoring each of these physiological characteristics are well known in the art and are available from a variety of manufacturers.

A current sleep state of the subject is determined using the physiological signals (step 220). As described above, conventional sleep science distinguishes between five different stages of sleep: a rested wakeful stage, NREM stages 1, 2, and 3, and the REM stage. Each of these stages may be distinguished from one another by reading various physiological signals of the subject. According to an embodiment, the physiological signals may be processed using a set of basic signal conditioning algorithms (e.g., artifact recognition and rejection, band-pass filtering, and/or other signal conditioning algorithms). According to an embodiment, the sleep state of the subject may be determined using well-known pattern recognition techniques to match the physiological signals obtained from the subject with one of the sleep stages described above.

The current sleep state information for the subject may then be added to a sleep state record associated with the subject (step 230). According to an embodiment, the sleep state record associated with the user is stored in a relational database or other persistent data store. The sleep state record for the user may also include a record of recent sleep information representing the sleep architecture of several most recent sleep episodes of the subject. The sleep architecture associated with the subject may be updated with the current sleep state for the subject at the end of each ongoing sleep episode.

A desired sleep state can then be determined by applying a set of rules to the current sleep information and the recent sleep information (step 240). The rules aid in optimizing the sleep performance of the subject by identifying a desired sleep state that the subject should be experiencing at a particular time. A set of rules may be defined for a particular subject and/or a particular set of sleeping parameters. For example, a parasomniac subject—i.e., a person who experiences abnormal and unnatural movements, behaviors, emotions, perceptions, and/or dreams during certain stages or sleep and/or during transitions between certain stages of sleep—may have a specific set of rules defined for that subject that limit the time that the subject remains in certain stages of sleep. In another example, a set of rules may be defined for a subject who is on a military deployment or working shift work, where irregular and abbreviated periods of sleep can occur. According to some embodiments, the rules may be defined as a set of IF-THEN rules. For example, if the subject has not slept for more than thirty minutes with at least twenty minutes of NREM Stage 2 sleep and the subject has not entered NREM Stage 3 sleep, then the desired stage sleep state is the current sleep state. According to some embodiments, the rules may be developed through initial monitoring of sleep patterns and/or the physiological characteristics of a subject and/or by providing various sensory stimuli to the subject during sleep to determine the subject's physiological and sleep pattern responses to those sensory stimuli during sleep. According to an embodiment, the personalization of the rules to suit the needs of the particular sleeper can include evaluating which physiological characteristics most clearly indicate a change between the sleeper's sleep states, which patterns of physiological characteristics occur at which portions of the sleeper's sleep cycle or under which circumstances, how a sleeper's physiological characteristics or sleep patterns change when exposed to sensory stimuli, how a sleeper's physiological characteristics respond when sleep is disrupted, optimal durations and patterns for a sleeper's sleep cycle, what sensory stimuli works most effectively to move the sleeper through the sleep stages, and/or other processes for calibrating the rules to the needs of a particular subject.

After the desired sleep state is determined using the rules, the desired sleep state may be compared to the current sleep state for the subject (step 250), and a determination can be made whether the current sleep state differs from the desired sleep state (step 260). If the current sleep state differs from the desired sleep state, sensory stimuli can be generated to guide the sleep pattern of the subject toward the desired sleep state (step 265). The sensory stimuli can be any stimuli that can be sensed by a sleeping subject. According to some embodiments, sensory stimuli may include light, sound, smell, vibration, heat or cold, moisture, electric shock, and/or other stimuli that can be sensed by a sleeper.

According to an embodiment, adjustments can be made to the sensory stimuli to lead the sleeping subject toward another sleep stage. These changes can include adjustments in the magnitude or quantity, tone, quality, pattern, frequency, application location, or any other adjustment to sensory stimuli. Even minute changes to sensory stimuli may be sufficient to lead the sleeping subject toward another sleep stage. The type, duration, intensity, and timing of generated stimuli depend on the current and desired sleep state and on whether a direct transition is physiologically possible or whether the sleeper needs to be led through some intermediate sleep state(s) prior to reaching the desired state. For example, if the sleeper is awake while the desired state is NREM Stage 2 sleep, soothing sounds may be generated to induce a transition from wakefulness through NREM Stage 1 sleep to NREM Stage 2. If for an example the sleeper is in NREM Stage 3 sleep while the desired state is NREM Stage 2 sleep, a combination of subliminal sounds and stroboscopic light flashes may be optimal. Continued monitoring of the physiological attributes of the subject can be used to determine whether the intended transition from one stage to sleep to another has taken place.

According to some embodiments, if the current sleep state does not differ from the desired sleep state, then no stimuli are generated to guide the sleep pattern of the subject, because the subject is already in an optimal sleep stage. According to other embodiments, if the current sleep state of the subject matches the desired sleep state, one or more stimuli may be generated to help maintain the current sleep state of the subject.

Disturbances that may interrupt or negatively impact the sleep state of the subject may be identified (step 270), and a determination can be made as to whether any disruptive disturbances are present (step 275). Disturbances may include loud noise, strong light, temperature of the sleeping environment, and/or any other potential distracters which may cause the subject to wake up frequently or prematurely or prevent the subject from spontaneously entering into deeper stages of sleep. If disruptive disturbances are present and identified, the subject may be protected from the disturbances by taking or initiating remedial actions. For example, if too much ambient light is present in the environment, the lights in the sleeping environment can be dimmed or the blinds closed to block sunlight or other light from outdoors from entering the room, or an eye mask or set of tinted glasses may be provided to block ambient light from reaching the subject's eyes. If the temperature of the room is too hot or too cold, a heating and ventilation system for the sleeping environment can be adjusted to adjust the temperature of the room to a more optimal sleeping temperature. If too much noise is present, a set of noise canceling headphones or earplugs may be provided, or white noise may be generated to block out the noise. If no disturbances are identified or the subject has been protected from the disturbances, the method returns to the monitoring step (step 210).

Figure 3:
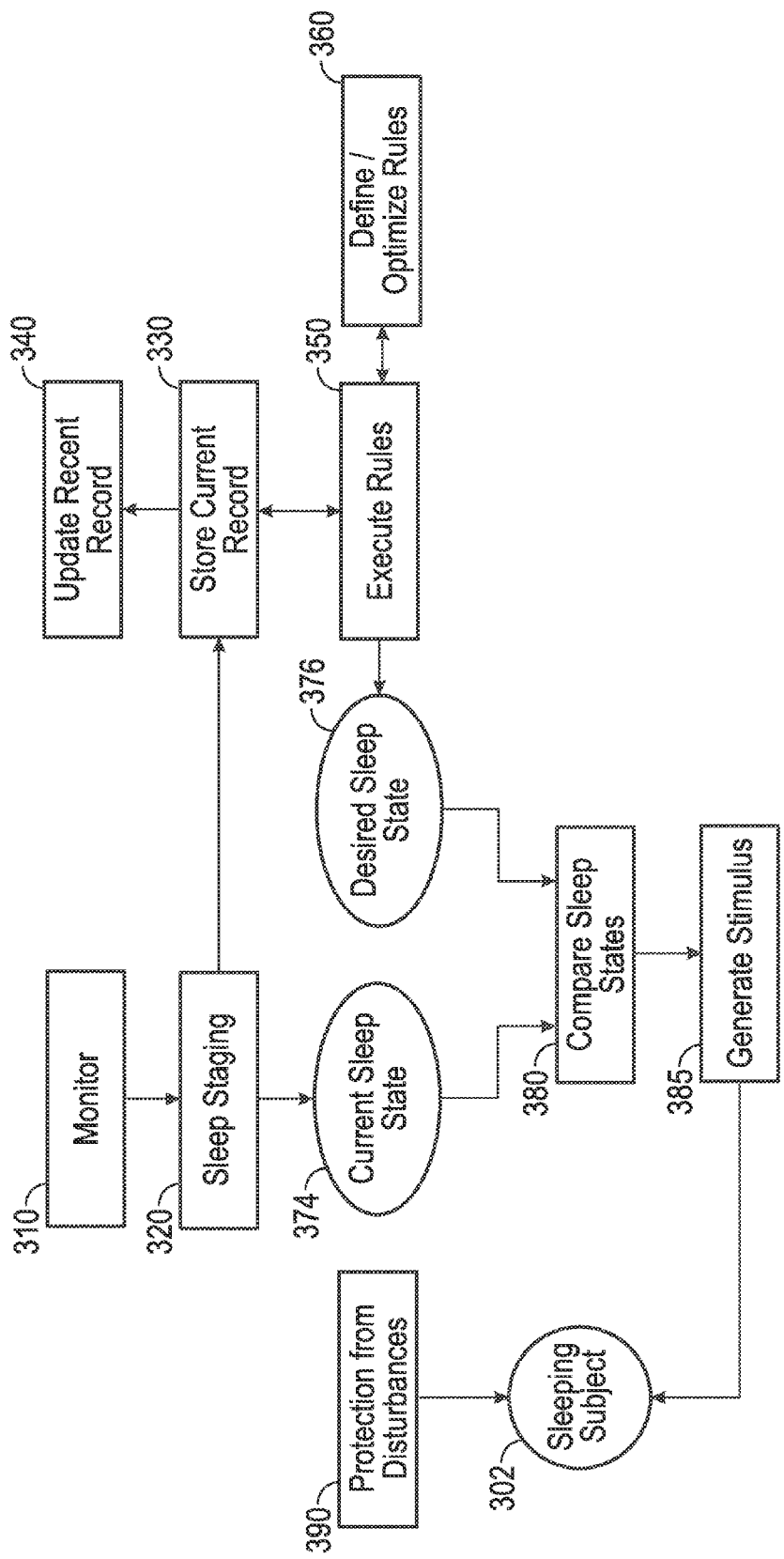
FIG. 3 illustrates a block diagram illustrating the logical components of a sleep guidance system, according to an embodiment.

FIG. 3 is a block diagram that illustrates the interaction of various functional components of a sleep guidance system, according to an embodiment. In one embodiment, this system carries out the method described in connection with FIG. 2. Monitor module 310 monitors one or more physiological signals indicative of sleep state of the sleeping subject 302 (similar to step 210 of FIG. 2). As described above, various signals can be monitored, such as but not limited to, electroencephalogram (EEG), electrooculogram (EOG), electromyogram (EMG), respiration, heart rate, body movement, galvanic skin reaction, blood pressure, blood flow, blood chemistry, behavioral responses, or some combination thereof. The monitor module 310 receives signals from various sensors and/or monitoring equipment (not shown). Such sensors and/or monitoring equipment are well known in the art. Therefore detailed descriptions of these sensors and/or monitoring equipment have been omitted. The monitor component 310 outputs physiological data received from the various sensors and/or monitoring equipment, and this physiological data is input into sleep staging component 320.

According to an embodiment, sleep staging component 320 implements basic signal conditioning algorithms for cleaning up the physiological data received from the monitoring component 310. For example, artifact recognition and rejection, band-pass filtering, and other conditioning algorithms may be executed on the physiological data by the sleep staging component 320. The sleep stating component 320 may also implement pattern recognition techniques for identifying patterns in the physiological data that can be used to detect a current sleep state of the subject 302 (similar to step 220 of FIG. 2). As described above, a subject typically exhibits specific physiological attributes during each stage of sleep that can be used to determine the current state of sleep that the subject is experiencing. Sleep staging component 320 outputs the current sleep state data 374 derived from the physiological data received from the monitoring component 320. The current sleep state data 374 represents a current stage of sleep that the sleeping subject 302 is experiencing.

The current sleep state is also provided to store current record component 330, which may write the current sleep data 374 to a sleep data store, such as a persistent memory (similar to step 230 of FIG. 2). According to an embodiment, the persistent data store may be implemented as a relational database that associates the current sleep data 374 with the subject. The information in the sleep data store can be later used to derive various descriptors of the sleep episode that can be, but are not limited to, total sleep time, time spent in each sleep state, percentage of each sleep state, position along a sleep cycle, and/or other information.

At the end of each sleep episode (when the subject 302 wakes), the update recent record component 340 may update the information about the sleep architecture of the several most recent sleep episodes of the subject (similar to step 230 of FIG. 2). This sleep architecture information may be stored in the sleep data store.

Execute rules module 350 may execute a set of rules on the information in the sleep data store including the data output from the store current record component 330 and the update recent record 340 to determine a desired sleep state that the subject should be experiencing in order to optimize the sleeping experience (similar to step 240 of FIG. 2). As described above, the rules that are executed may be customized for different subjects and/or sleeping situations or environments. The execute rules module 350 outputs desired sleep state data 374 that represents a desired sleep state that the sleeping subject 302 should be experiencing according to the rules.

Compare sleep states module 380 compares the current sleep state data 374 with the desired sleep state data 376 (similar to step 250 of FIG. 2). In an embodiment, if the current sleep state of the sleeping subject 302 differs from the desired sleep state, the compare sleep states module 380 identifies a set of stimuli that may be generated and applied to the subject 302 in order to guide the sleeping subject 302 from the current sleep state to the desired sleep state. The subject 302 may need to be guided through one or more intermediary sleep states in order to reach the desired sleep state.

The generate stimulus module 385 receives control signals from the compare sleep states module 380 that indicates the pattern of sensory stimuli that the generate stimulus module 385 should generate in order to guide the subject 302 to the desired sleep state (similar to step 265 of FIG. 2). According to an embodiment, the generate stimulus module 385 may also be instructed to generate sensory stimuli either at selected intervals or continuously throughout a sleep period so that the subject 302 reaches a sleep stage near an awake stage of the sleep cycle within a predetermined period of time at the end of the sleep period. For example, if the subject 302 needs to awaken at 6:00 am, the generate stimulus module 385 may generate stimuli to guide the subject 302 toward reaching an awake state between 5:45 am and 6:00 am. By guiding the subject 302 toward an awake state prior to waking the subject 302, the subject may wake more refreshed and with lesser impact from sleep inertia. According to some embodiments, the generate stimulus module 385 may also be instructed to generate at least one sensory stimulus to cause the sleeper to remain in the current sleep state, and the stimulus generator may be configured to generate the at least one sensory stimulus to cause the sleeper to remain in the current sleep state. For example, if the subject 302 has already reached NREM Stage 3 and NREM Stage 3 is the desired sleep stage for the subject 302, the generate stimulus module 385 may generate one or more stimuli that encourage the subject 302 to remain in NREM Stage 3.

The define and optimize rules module 360 provides an interface that enables the rules, to be executed by execute rules module 350, to be defined, modified, and/or deleted. According to an embodiment, the define and optimize rules module 360 provides a graphical user interface, such as a web page or executable application, that enables a user to define new rules and modify or delete existing rules. According to an embodiment, the define and optimize rules module provides an interface for receiving input for creating and/or modifying rules from computer systems and/or various instruments for monitoring the physiological attribute of the subject 302.

According to an embodiment, protection from disturbances module 390 identifies potential distracters in the operational environment, such as loud noise, strong light, high or low temperatures, or other environmental conditions that may cause the subject to wake prematurely or may prevent the subject from spontaneously entering into deeper stages of sleep (similar to step 270 of FIG. 2). Automatic and/or manual steps may be taken to attenuate or block potential distracters (similar to step 280 of FIG. 2). The protection from disturbances module 390 can automatically take steps to attenuate or block the potential distracters, such as dimming lights, adjusting the temperature of a heating and cooling system, performing active noise cancellation, and the like. According to some embodiments, manual steps may also be taken to attenuate or block the potential distracters, such as placing a mask or dark glasses on the subject to block light, provide earplugs or headphones to the subject to block and/or attenuate noise, and the like. According to some embodiments, the protection from disturbances module 390 may alert either the subject or an attendant (depending upon the operational environment) to take one or more manual steps to attenuate or block the potential distracters, or initiate such steps automatically (i.e., without human intervention) by interfacing or otherwise communicating with one or more controls that are able to attenuate or block the potential distracters, for example, using electronic means.

System Overview

Figure 4:
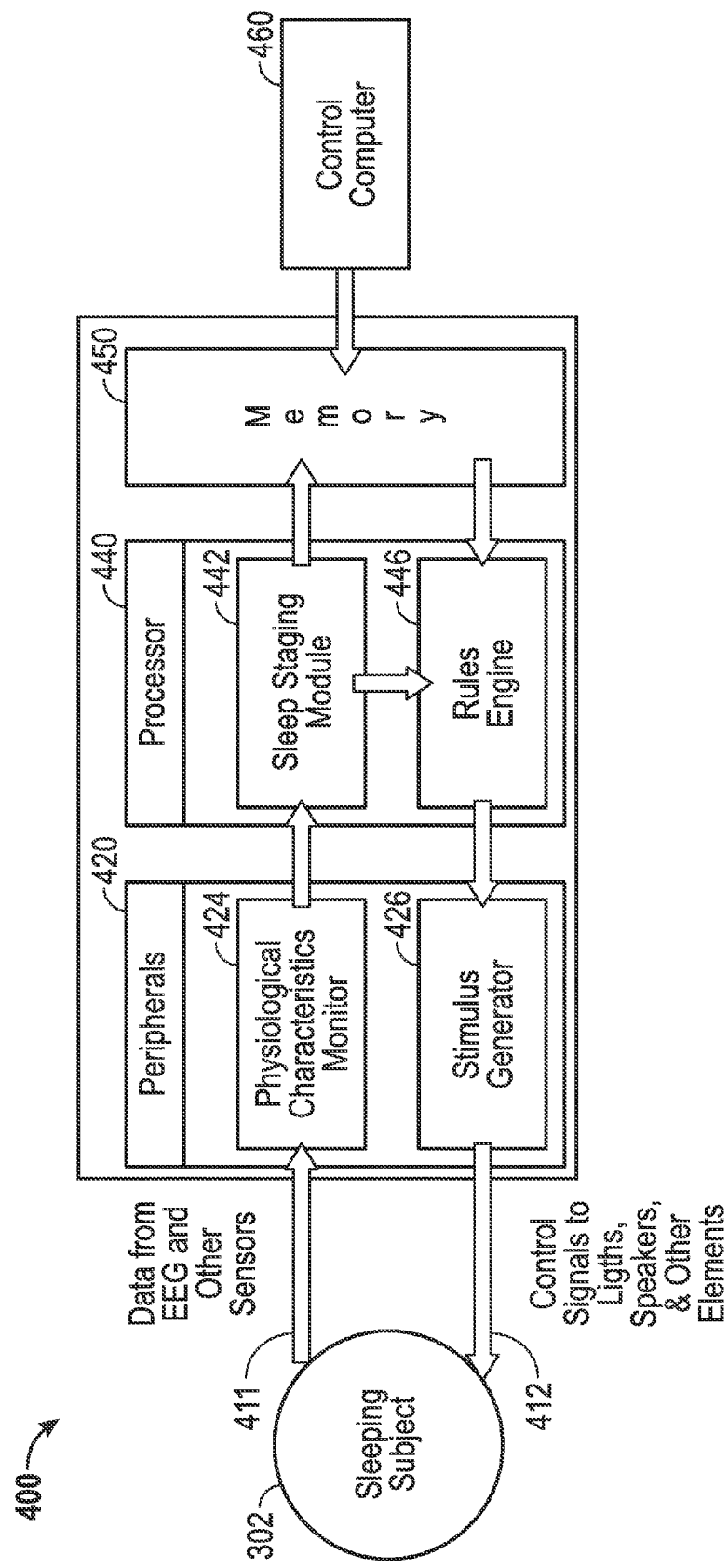
FIG. 4 illustrates a high level block diagram of a sleep guidance system, according to an embodiment.

FIG. 4 illustrates an exemplary sleep guidance system 400, according to an embodiment. Sleep guidance system 400 includes a data processor 440. System 400 is an example of one possible configuration of software and/or hardware that may be used to implement the method illustrated in FIG. 2 and the functional components of a sleep guidance system illustrated in FIG. 3. According to an embodiment, data processor 440 comprises a computer system that includes one or more microprocessors for executing instructions, such as a personal computer system, laptop computer, or server. Data processor 440 controls the operation of the sleep guidance system 400 to guide a subject 302 through one or more sleep cycles. The data processor 440 is configured, through hardware, software or both, to communicate with each of a number of associated peripherals 420.

Data processor 440 includes a sleep staging module 442 and rules engine 446. Sleep staging module 442 receives physiological data output by physiological characteristics monitor 424.

According to an embodiment, sleep staging module 442 implements basic signal conditioning algorithms for cleaning up the physiological data received from the physiological characteristics monitor 424. For example, artifact recognition and rejection, band-pass filtering, and other conditioning algorithms may be executed on the physiological data by the sleep staging module 442. The sleep staging module 442 also implements pattern recognition techniques for identifying patterns in the physiological data that can be used to detect a current sleep state of the subject 302.

Rules engine 446 executes rules, such as those described above with respect to step 250 of FIG. 2, to determine a desired sleep stage for the subject which can then be used to determine the types of stimulus that the stimulus generator 426 of peripherals 420 should generate.

Stimulus generator 426 can generate various control signals 412 that control various peripherals that apply various stimuli to subject 302, such as those described above with respect to step 265 of FIG. 2. For example, the stimulus generator 426 may generate control signals that control lights, speakers, and/or other devices that generate stimuli such as light, sound, and changes in temperature.

Data processor 440 may be configured differently for each embodiment of the invention to enable the various sleep guidance rules and to coordinate monitoring of physiological signals, interpreting of the physiological data received, mapping the sleep patterns and physiological signals of the sleeper throughout the sleep cycle, determining of a sleeper's current sleep state, identifying which physiological characteristics indicate when a sleeper is about to transition to a new sleep state and which sensory stimuli characteristics will guide the sleeper to transition to a new sleep state, and generating sensory stimuli to guide the sleeper to the new sleep state.

Sleep guidance system 400 includes one or more peripherals 420 operatively coupled to data processor 440 to provide various stimuli for guiding the sleep of the subject 302 and for monitoring various physiological characteristics of the subject 302. For example, physical characteristics monitor 424 can receive signals 411 from various sensors used to detect physiological characteristics of subject 302. According to some embodiments, the sensors include electroencephalographs, electrooculograms, electromyograms, microphones, motion sensors, moisture sensors, blood pressure cuffs, thermistors or nasal cannulas connected to a pressure transducer, pulse oximeters, thermometers or other temperature sensing devices, and/or any other sensor that can detect a physiological characteristic of the subject 302.

Sleep guidance system 400 includes sensory stimulus generator 426 operatively coupled to data processor 440. The sensory stimulus generator 426 provides sensory stimuli to the sleeping subject 302. The sensory stimulus generator 426 includes at least one stimuli source device used to generate stimuli that may be perceived by the sleeping subject 302 through the subject's senses. According to an embodiment, the stimuli source devices can include speakers, vibrators, lights, electric contacts, fans, heaters, coolers, and/or other devices that can generate stimuli that may be perceived through the sleeping subject's senses. The stimulus generator 426 can include various components for providing sensory stimuli to the sleeping subject 302. According to an embodiment, the components of the stimulus generator 426 can include ear phones, a mask that fits over the eyes and/or face of subject 302, a headband, a belt, a wristband, a ring, and/or other components that enable the stimulus source devices to convey stimuli to the subject 302.

Sleep guidance system 400 also includes memory 450. Memory 450 is a computer-readable memory, such as a read-only memory (ROM), random-access memory (RAM), a flash memory, magnetic media memory, and/or other memory for storing data to be used by and/or generated by sleep guidance system 400 and/or executable program code that may be executed by data processor 440.

According to some embodiments, a control computer system 460 is used to program data processor 440 of the sleep guidance system 400. Control computer system 460 can be used to define rules for determining desired sleep states and/or to personalize sleep profiles. Alternatively, that functionality can be implemented by the processor 440 coupled with appropriate user interface peripherals. Various types of computer systems may be used for control computer system 460, such as a personal computer system, a laptop computer system, a handheld computer system, or the like. According to an embodiment, the sleep guidance system 400 provides a graphical user interface, such as a web page or executable application, that enables a user to define new rules and modify or delete existing rules. According to an embodiment, the sleep guidance system 400 provides an interface for receiving input for creating and/or modifying rules from computer systems and/or various instruments for monitoring the physiological attribute of the subject 302.

One embodiment of the sleep guidance system 400 is for use in operational environments, such as in shift work environments where workers are working shifts that disrupt typical sleep patterns or on military field deployments where personnel in the field may experience extended periods of disrupted sleep patterns. The signals 411 used for monitoring and determining the sleeper's sleep states comprise EEG recorded from the forehead using dry electrodes, two modified EOG channels (left and right epicanthus referenced to nasion) and head movements recorded with an accelerometer. According to an embodiment, the stimulus generator 426 includes thick, yet soft, ear covers that provide attenuation of environmental noise, and embedded ear pads with small speakers to deliver audio stimulation to the subject 302. According to an embodiment, a thick and soft eye mask or a set of non-transparent glasses serve to block out environmental light. According to some embodiments, the eye mask or glasses house one or more light emitting elements that provide visual stimulation, and according to some embodiments, the eye mask or the glasses include one or more heating and/or cooling elements. The rules used by rules engine 446 for determining desired sleep states are configured to balance the sleep cycle of the subject 302 to create a balance between NREM Stage 2, NREM Stage 3, and REM stage sleep over long periods of time, such as a couple of days, and to gradually wake up the subject 302 when required so as to avoid significant sleep inertia that can impair the post-sleep performance of the subject 302. Aspects of this embodiment include portability, light-weighted-ness, simplicity, and/or protection from environmental disturbances.

Another embodiment of the sleep guidance system 400 is for use in the treatment of parasomnias secondary to a psychiatric condition. In this embodiment, the rules used by rules engine 446 to drive the stimulus generator 426 are defined to create stimuli that cause the sleeping subject 302 to not enter sleep states in which nightmares, bed wetting, or sleepwalking can occur.

FIG. 4 merely illustrates one possible configuration of a sleep guidance system. Different combinations of elements can be used to adapt the sleep guidance system to various environments, such as hospitals, homes, businesses, and field deployments. According to some embodiments, the attenuation of environmental disturbances is not required, because the sleeping subject is expected to use the sleep guidance system in the subject's home or in a hospital room where environmental disturbances are less likely.

Figure 5:
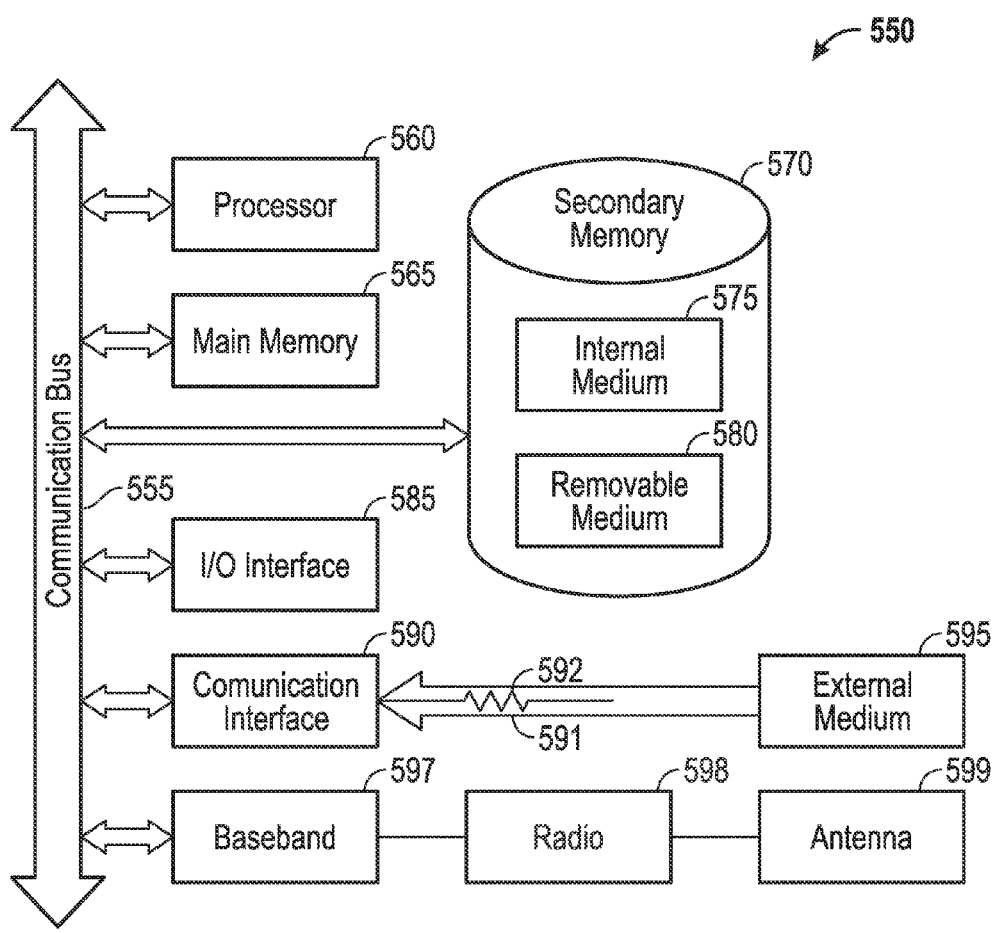
FIG. 5 illustrates an example processing device on which one or more of the processes described herein may be executed, according to an embodiment.

FIG. 5 is a block diagram illustrating an example wired or wireless system 550 that may be used in connection with various embodiments described herein, according to an embodiment. For example the system 550 may be used as or in conjunction with or as components of one or more of the mechanisms, processes, or devices described elsewhere herein, including those components illustrated in FIGS. 4 and/or 6. As will be clear to those skilled in the art, alternative processor-enabled systems and/or architectures may also be used.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Perl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 592. These signals 592 are preferably provided to communication interface 590 via a communication channel 591. In one embodiment, the communication channel 591 may be a wired or wireless network, or any variety of other communication links. Communication channel 591 carries signals 592 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 599, a radio system 598 and a baseband system 597. In the system 550, radio frequency (RF) signals are transmitted and received over the air by the antenna system 599 under the management of the radio system 598.

In one embodiment, the antenna system 599 may comprise one or more antennae and one or more multiplexors (not shown) that perform a switching function to provide the antenna system 599 with transmit and receive signal paths. In the receive path, received RF signals can be coupled from a multiplexor to a low noise amplifier (not shown) that amplifies the received RF signal and sends the amplified signal to the radio system 598.

In alternative embodiments, the radio system 598 may comprise one or more radios that are configured to communicate over various frequencies. In one embodiment, the radio system 598 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 598 to the baseband system 597.

If the received signal contains audio information, then baseband system 597 decodes the signal and converts it to an analog signal. Then the signal is amplified and sent to a speaker. The baseband system 597 also receives analog audio signals from a microphone. These analog audio signals are converted to digital signals and encoded by the baseband system 597. The baseband system 597 also codes the digital signals for transmission and generates a baseband transmit audio signal that is routed to the modulator portion of the radio system 598. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 599 where the signal is switched to the antenna port for transmission.

The baseband system 597 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 597 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Example Embodiment

In an embodiment, a method for optimization of performance through napping may comprise: (1) tracking of accumulated sleep debt; (2) assessment of sleep quality for each nap; and (3) to the extent possible, tailoring the sleep architecture for each nap by natural (i.e., non-pharmacological) means. In an embodiment, a system which integrates these three aspects and optimizes napping in difficult operational environments may comprise a light-weight, battery-powered device that is worn like a sleep mask. This device may be configured to: (1) assess sleep in real time by measuring electrical activity in the brain using sensors (e.g., electroencephalographic (EEG) sensors) placed on the forehead; (2) maintain a record of all naps taken and use the record (e.g., in conjunction with a built-in clock) to estimate the accumulated sleep debt; (3) provide protection from ambient disturbances (e.g., excessive light and/or loud noise); (4) deliver auditory, visual, and/or thermal stimuli to influence the sleep architecture of each nap; and/or (5) awaken the subject at an appropriate time to avoid sleep inertia or minimize its effects on post-nap performance.

Figure 6:
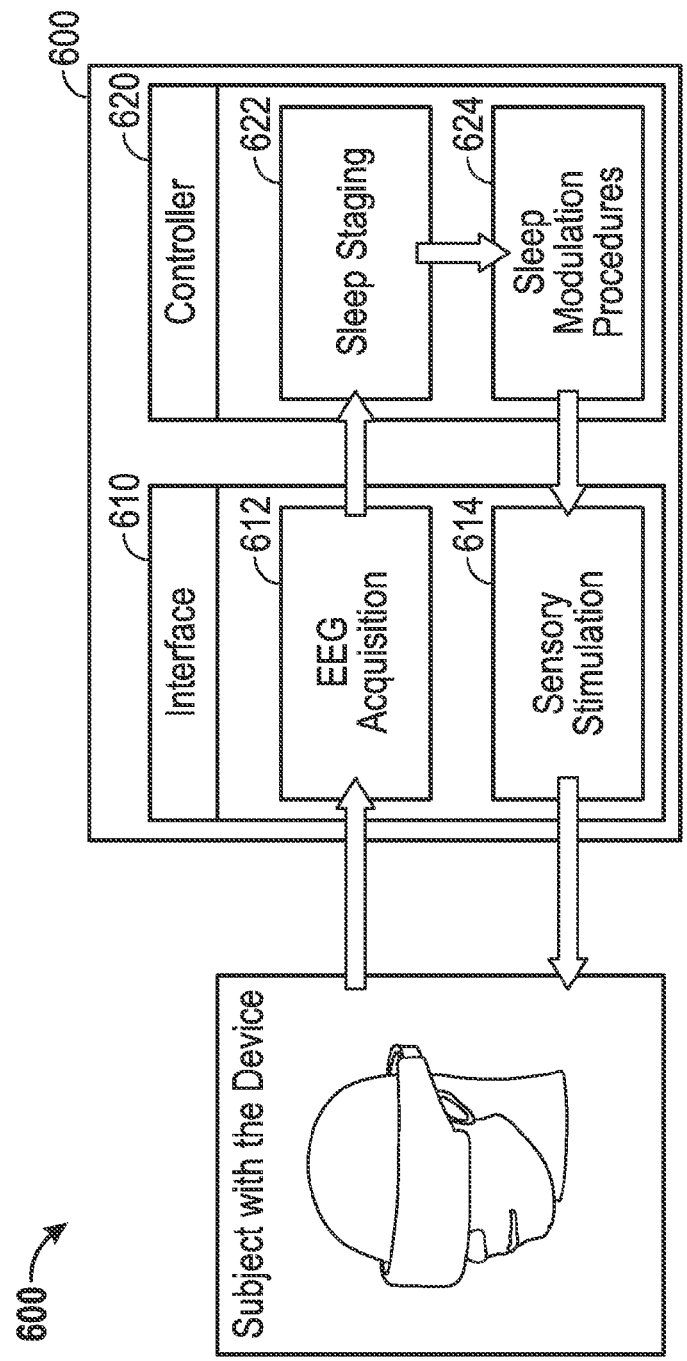
FIG. 6 illustrates an example device that can be used to tailor a sleep architecture, according to an embodiment.

FIG. 6 illustrates a software architecture of such a device, according to an embodiment. The architecture illustrated in FIG. 6 may be implemented, for instance, in the system shown in FIG. 4 and/or FIG. 5. Device 600 comprises an interface 610 and controller 620. In turn, interface 610 comprises EEG acquisition module 612 and sensory stimulation module 614, and controller 620 comprises sleep staging module 622 and sleep modulation module 624. EEG acquisition module 612 of interface 610 receives one or more EEG signals from EEG sensors of device 600, and outputs EEG data to sleep staging module 622. Sleep staging module 622 utilizes the signals received from EEG acquisition module 612 to determine, for example, the current sleep stage and desired sleep stage for the subject, and passes this data to sleep modulation module 624. Sleep modulation module 624 may apply one or more rules or procedures to determine a strategy for implementing a desired sleep architecture for the subject based, at least in part, on the current and desired sleep stages, as well as other information (e.g., recent sleep stages, a desired wake-up time, etc.). Based on this determined strategy, sleep modulation module 624 may instruct or control sensory stimulation module 614 to generate one or more stimuli to be applied to the subject by the device.

In an embodiment, the device (e.g., device 600) comprises or connects to and interfaces with a sleep mask that comprises one or more sensors (e.g., EEG sensors which feed the EEG acquisition module 612) and/or one or more elements which apply stimuli to the subject wearing the device. In such an embodiment, the system comprising the device and sleep mask allows for sleep staging and sleep debt tracking using real-time analysis of the sensors, which may comprise EEG sensors positioned on the forehead of the subject and/or providing EEG signals from the forehead of the subject. The system may also provide protection from ambient light and noise by constructing the mask such that it covers the subject's eyes and ears, and comprises elements (e.g., speakers) which provide active noise reduction. In addition, the system may optimize sleep quality by providing stimuli, such as facial heat, through the sleep mask in order to promote the onset and consolidation of sleep. Furthermore, the system may allow for awakening a subject without sleep inertia by providing a stimulus, such as blue light, through the sleep mask prior to and shortly after awakening.

One way to assess sleep quality is to record the electrical activity of the brain by means of EEG. However, standard passive wet EEG electrodes are impractical for long-term use in the field, and dry sensors are bulky, uncomfortable to sleep with, and sensitive to noise. Thus, for certain embodiments, a hybrid sensor that is small and soft (i.e. passive), yet durable, was developed. In an embodiment, the hybrid sensor is made of conductive spacer fabrics filled with semi-dry hydrogel with dissolved salts, as described in greater detail below. These hybrid EEG sensors may then be integrated with one or more modalities of sensory stimulation (e.g., visual, thermal, and audio) into a comfortable sleep mask. In addition, analog and digital circuits may be integrated into the light-weight, wearable device to support EEG acquisition, real-time sleep staging, and various paradigms of the sensory stimulation.

Figure 7:
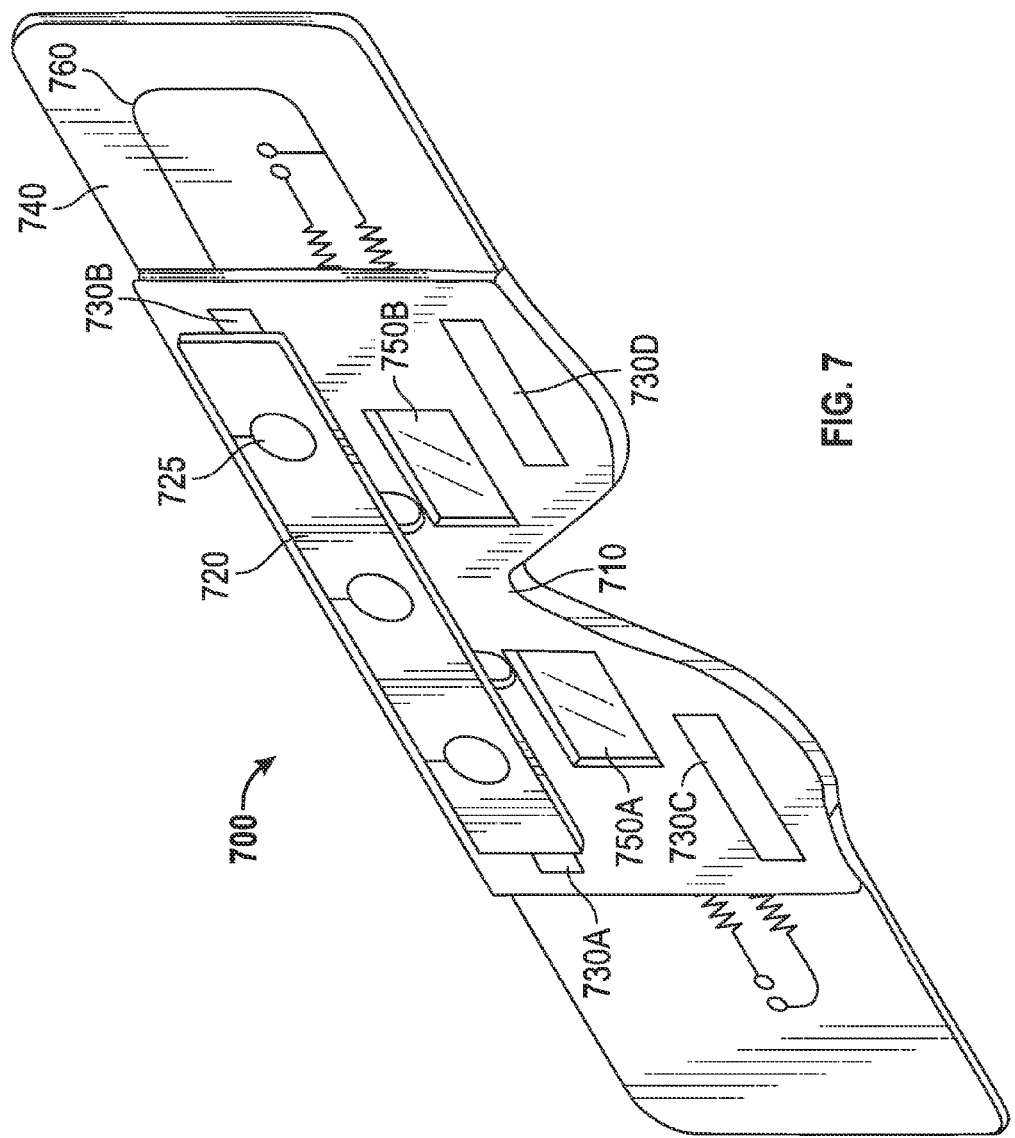
FIG. 7 illustrates an example sleep mask that can be used to collect physiological signals from a subject and deliver sensory stimuli to the subject, according to an embodiment.

As illustrated in FIG. 7, in an embodiment, the sleep mask may be a soft sleep mask 700 comprising multiple layers of conductive textile. For instance, the sleep mask may consist of the following seven layers:

(1) Interior (facial) cover 710. In an embodiment, interior cover 710 is made of a non-conductive polyester blend. The interior cover 710 may comprise two interior cuts (e.g., rectangular cuts) for the eyes.

Figure 8:
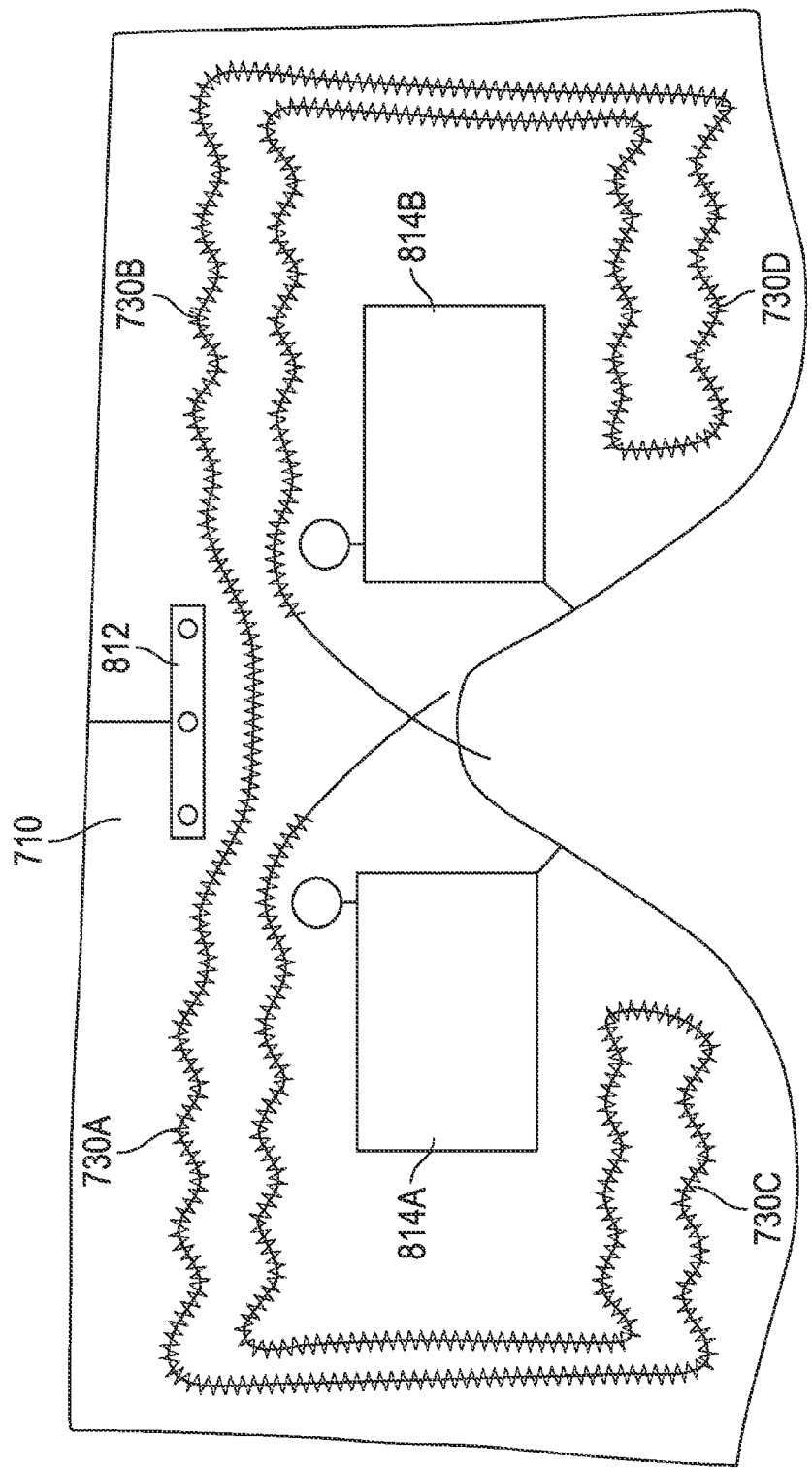
FIG. 8 illustrates a layer of the sleep mask in FIG. 7, comprising embroidered conductive thread, according to an embodiment.

(2) EEG sensor layer 720. In an embodiment, EEG sensor layer 720 is made of conductive thread embroidered onto non-stretch pongee fabric. Conductive loop rounds may be sewn to each EEG sensor site 725 using the conductive thread. FIG. 8 illustrates interior cover 710, which has sensor attachment site 812. As illustrated, sensor attachment site 812 may comprise conductive thread which conductively interfaces with attachment elements (e.g., snap halves). In an embodiment, the conductive thread, which acts as a substitute for EEG wire leads, is silver-coated and/or has an electrical resistance of less than 4 ohms per inch, and may have excellent noise characteristics. EEG sensor layer 720 may be attached or otherwise connected to sensor attachment site 812 using corresponding attachment elements (e.g., snap halves). The attachment elements or other elements may provide a conductive coupling between the conductive thread of sensor attachment site 812 and the conductive thread of EEG sensor sites 725, thereby providing conduction between EEG sensors conductively attached to EEG sensor sites 725 and sensor attachment site 812. It should be understood that the connection between EEG sensor layer 720 and sensor attachment site 812 may be releasable or fixed, and may utilize corresponding releasable elements, corresponding fixed elements, or a single element that holds EEG sensor layer 720 to sensor attachment site 812. In embodiments, in which the connection is releasable, EEG sensor layer 720 may be detached and replaced with another EEG sensor layer or reused with another sleep mask 700.

(3) Heater 730. In an embodiment, heater 730 is made of conductive thread insulated in plastic sheeting, and embroidered to a non-stretch textile, such as interior cover 710. In an embodiment, the conductive thread is silverized. FIG. 8 illustrates silverized, insulated, conductive thread embroidered into interior cover 710 to provide heating element(s) 730.

(4) Insulating foam 740. In an embodiment, insulating foam 740 comprises polyurethane foam cut to the shape of sleep mask 700 and/or positioned between interior layer 710 and audio layer 760. Insulating foam 740 may be one-quarter inch thick with two interior cuts (e.g., rectangular cuts) for the eyes and one or more interior cuts for the device snaps (e.g., that connect EEG sensor layer 720 to interior cover 710). Insulating foam 740 may also comprise cuts (e.g., oval cuts) at speaker sites, so as not to obscure auditory stimulation from audio layer 760. The role of insulating foam layer 740 is to keep the heat in—i.e., to reduce the transfer of heat from heater 730 through the exterior layers to the air—in order to optimize power consumption of the system.

Figure 9:
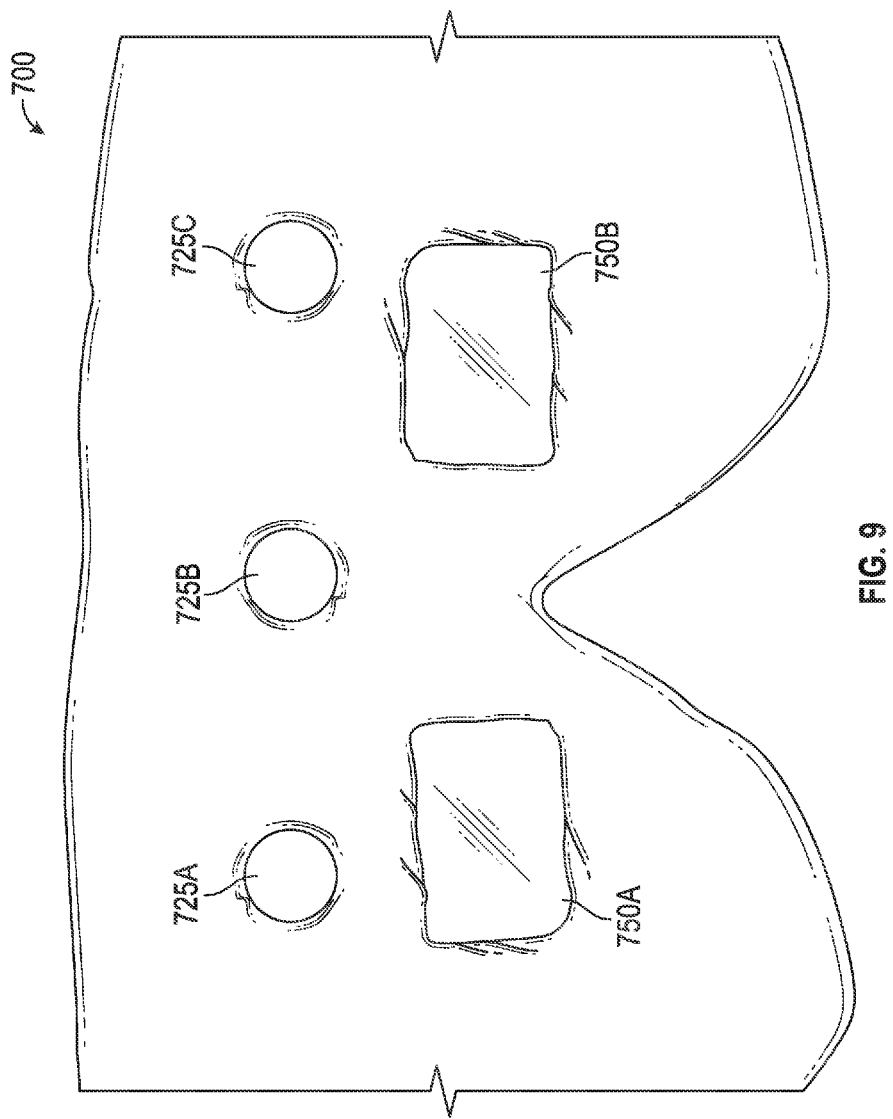
FIG. 9 illustrates a sleep mask with hybrid sensors and electroluminescent panels, according to an embodiment.

(5) Electroluminescent lamp sheets or panels 750. Electroluminescent lamp panels 750 are configured to provide visual stimulation to a subject wearing the system. In an embodiment, electroluminescent lamp panels 750 are washable and flexible and may be laminated and sewn to an embroidered bus layer (e.g., embroidered into interior cover 710). For example, electroluminescent lamp panels 750 may be electrically coupled to conductive threads 814 embroidered into interior cover 710. Conductive threads 814 may be silver-coated and/or have an electrical resistance of less than four ohms per inch, with excellent noise characteristics. As a single illustrative, non-limiting example, electroluminescent lamp panels 750 may comprise electroluminescent sheets produced by Electro Luminescence, Incorporated, of Aromas, Calif. Similar battery-powered and durable technology has been used in applications such as consumer apparel and textile, safety lighting on life vests and jackets, and backlight panels for membrane switches in hand-held devices such as cell phones and calculators. FIG. 9 illustrates electroluminescent lamp panels 750, integrated into sleep mask 700, along with EEG sensors 725.

Figure 10:
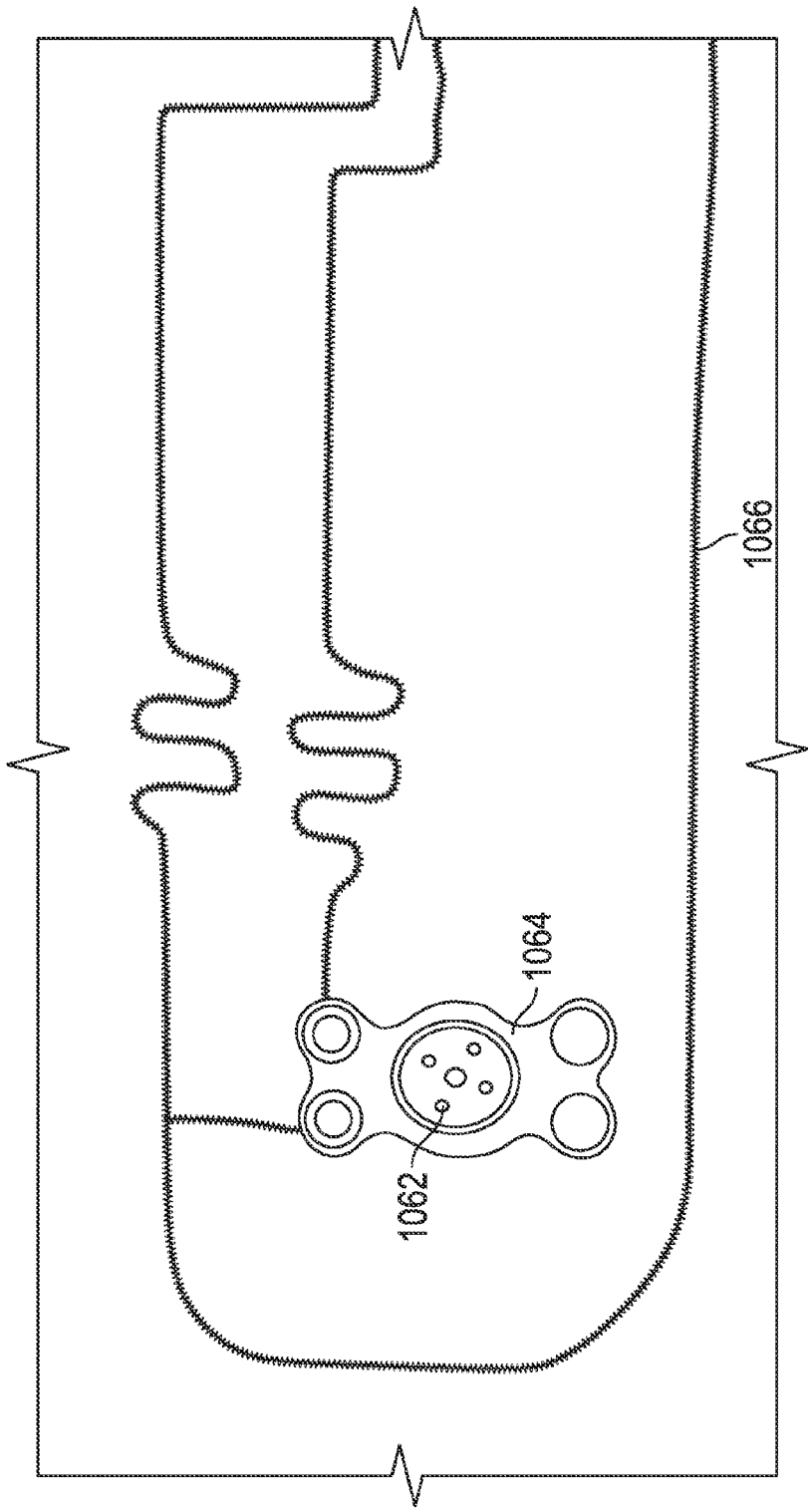
FIG. 10 illustrates an audio layer of a sleep mask, according to an embodiment.

(6) Audio layer 760. In an embodiment, illustrated in FIG. 10, audio layer 760 comprises speakers 1062 soldered to a flex 1064 and sewn with conductive thread to an embroidered bus 1066 on stretch fabric. Speakers 1062 may be small, i.e., ten millimeters or smaller in diameter. As a single illustrative, non-limiting example, speakers 1062 may comprise 0.15 watt Kobitone™ speakers (e.g., Kobitone Part No. 254-DS108-RO). Speakers 1062 may be soldered onto flex 1064, such as a DuPont™ Kapton™ flex, which may be custom-made. Speakers 1062 may also be embedded into the thermal insulating foam, such as insulating foam 740. The conductive threads utilized in audio layer 760, which act as audio leads, may be silver-coated, and have an electrical resistance of less than one ohm per inch, with excellent noise characteristics.

(7) Exterior cover (not shown). In an embodiment, an exterior cover is provided, and may comprise polyester blend fabric with cuts for attachment sites which are configured to attach sleep mask 700 to device 600 via corresponding attachment sites on device 600. For example, the exterior cover of sleep mask 700 may comprise round cuts for snap sites which are configured to attach to corresponding snap sites on device 600.

In the illustrated embodiment, sleep mask 700 measures 45 inches by 5 inches and is 0.75 inches thick. However, it should be understood that other dimensions are possible.

Device 600 and sleep mask 700 may be configured to releasably or fixedly attach to and interface with each other. For instance, device 600 and sleep mask 700 may be releasably connected and interfaced using corresponding stud halves (e.g., male stud halves corresponding to female stud halves) of one or more (e.g., nine) nickel-plated snaps similar to those used in garments (e.g., sports jackets). In such an embodiment, the snap portions on sleep mask 700 may be electrically coupled to conductive elements in sleep mask 700 (e.g., one or more of the various conductive threads described above, such as the conductive threads for the EEG sensor layer 720, heater 730, electroluminescent lamp panel(s) 750, and audio layer 760). Similarly, the corresponding snap portions on device 600 may be electrically coupled to conductive elements in device 600 (e.g., electrical traces coupled to EEG acquisition module 612 and sensory stimulation module 614). Thus, when fastened together (e.g., when male snap portions are fastened into corresponding female snap portions), the corresponding snap portions may create one or more electrical connections between the components of device 600 and sleep mask 700. For example, the electrical connections may comprise one or more electrical paths between EEG sensor layer 720 and EEG acquisition module 720, and one or more electrical paths between sensory stimulation module 614 and heater 730, electroluminescent lamp panel(s) 750, and audio layer 760. However, it should be understood that other connection and interface types which are well known in the art may be used, and that device 600 and sleep mask 700 may be positionally connected via one means and electrically or communicatively coupled via a different means, rather than positionally and electrically/communicatively connected via a single means (e.g., nickel-plated snaps).

For example, in an alternative embodiment, device 600 and sleep mask 700 may not be electrically coupled and/or positionally or physically coupled to each other. In this embodiment, device 600 and sleep mask 700 may be communicatively coupled via standard wireless communication protocols (e.g., Bluetooth™). In addition, device 600 and sleep mask 700 may each comprise its own power source (e.g., battery).

Figure 11A:
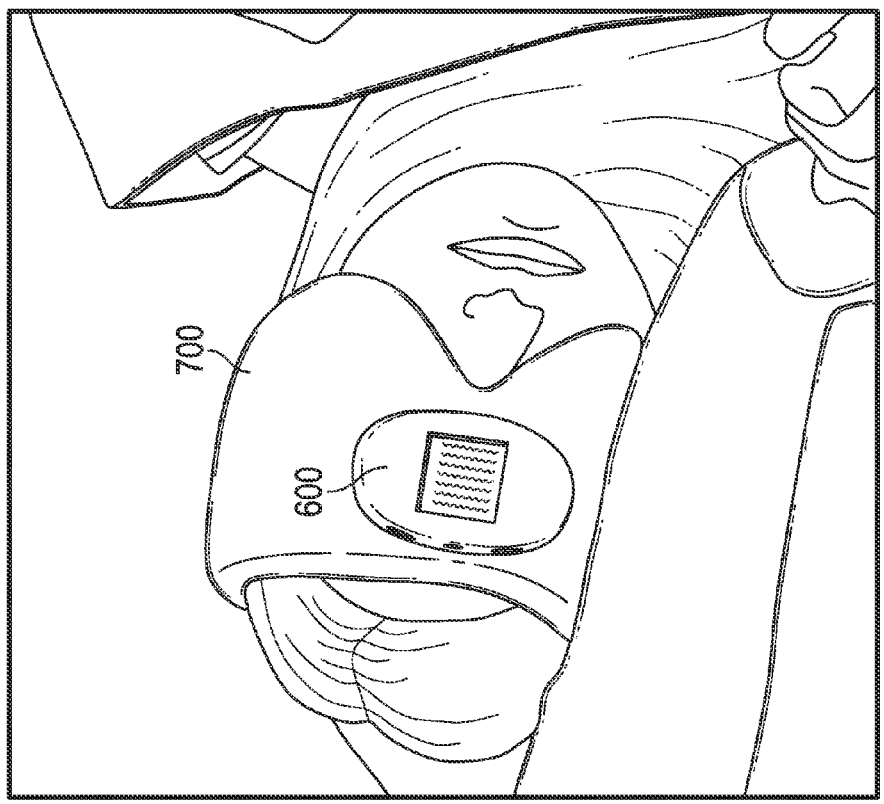
FIGS. 11A-11D illustrate embodiments of a releasably attachable sleep mask and device, according to embodiments.
Figure 11B:
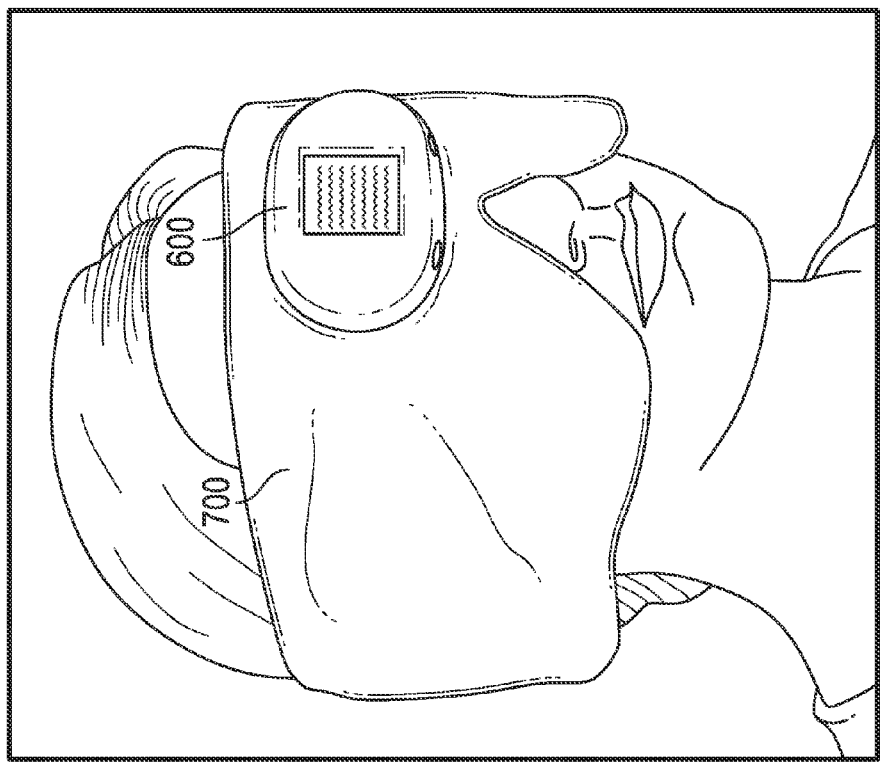
Figure 11C:
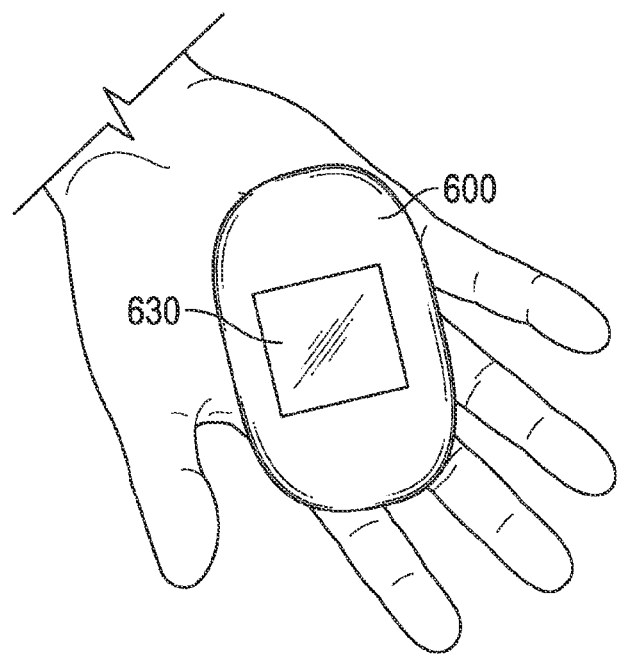
Figure 11D:
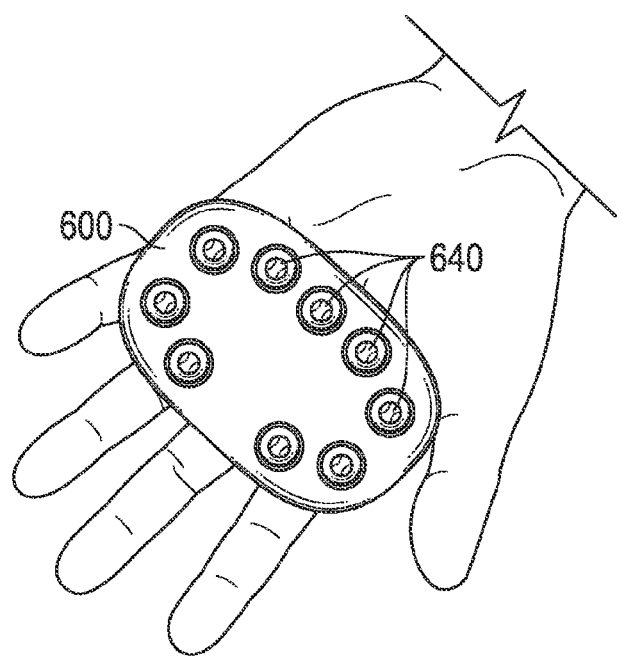

FIGS. 11A and 11B illustrate device 600 and sleep mask 700 connected to each other in various states of use, according to an embodiment. FIG. 11C illustrates the front of device 600, according to an embodiment. The front of device 600 may comprise a display 630, which can be controlled by controller 620 to display various information related to the subject and/or analysis being performed by device 600, including real-time information and reports. For example, display 630 may display instructions about how to use or apply device 600 and/or sleep mask 700, information about the monitored sleep states (e.g., current and/or past sleep states), information about desired sleep states, information about the subject, collected metrics and/or indexes, and the like. The information may be color-coded for ease of understanding and differentiation. Notably, device 600 is configured such that display 630 is faced outward when connected to sleep mask 700, such that display 630 is visible, even when the subject is wearing it. FIG. 11D illustrates the back of device 600, which may comprise one or more (e.g., nine) snap portions 640, which are configured to fasten to corresponding snap portion on sleep mask 700, as discussed above.

Figure 12:
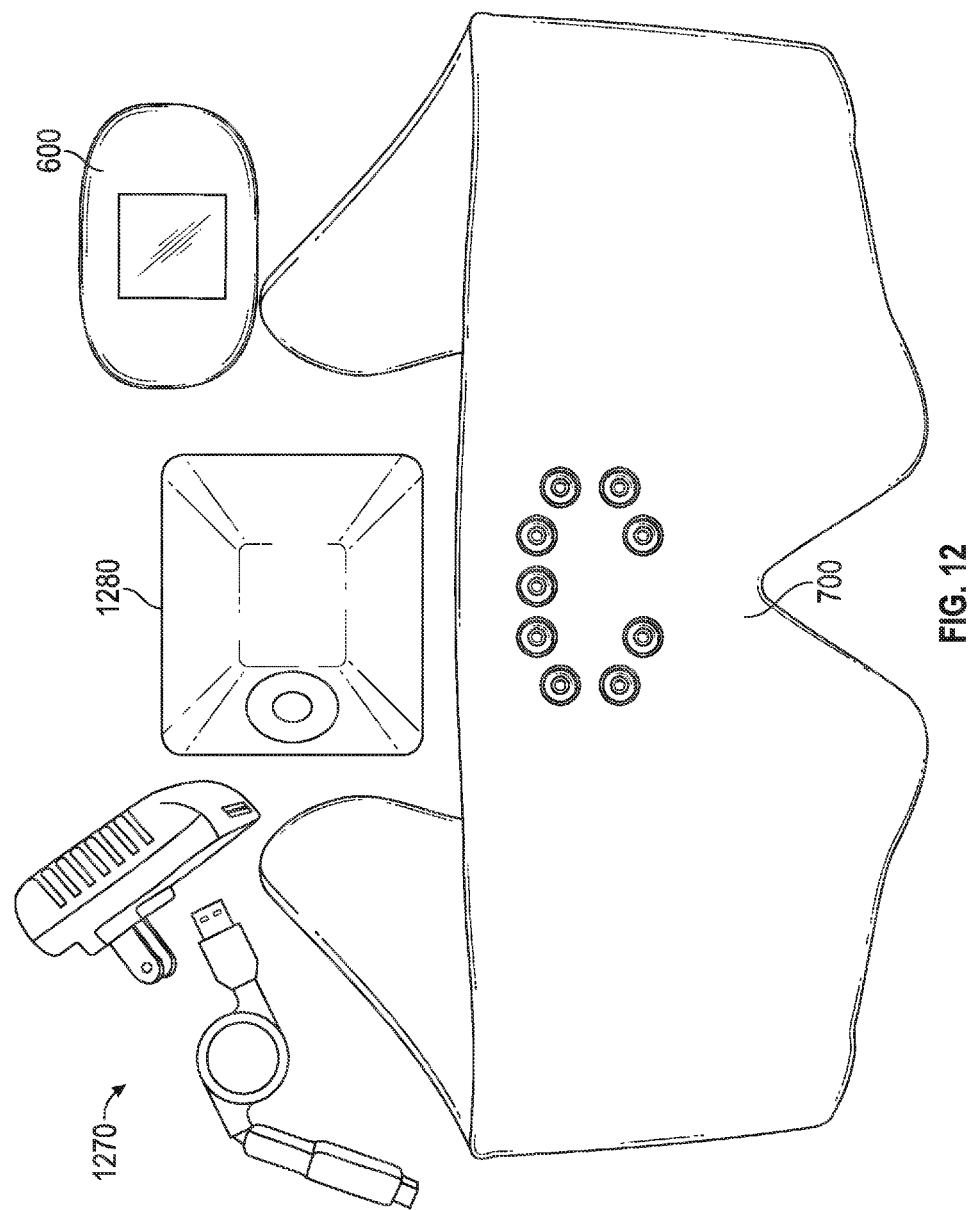
FIG. 12 illustrates a kit, comprising a system for tailoring a sleep architecture, according to an embodiment.

In an embodiment, device 600 and sleep mask 700 may be provided together in a kit. In an embodiment of such a kit is illustrated in FIG. 12. In addition to device 600 and sleep mask 700, the kit may comprise a charger 1270 (e.g., Universal Serial Bus (USB) and 110 Volt and/or 220 Volt connections) and/or a supplemental portable battery 1280 that can be used the charge a built-in battery of device 600 in the field when no other power source is available.

As mentioned above, an improved EEG sensor has been developed for use in embodiments of the disclosed system. In an embodiment, this hybrid EEG sensor comprises hydrogel grown into conductive spacer fabric. For instance, the hybrid EEG sensor may be created by growing poly-acrylic hydrogel into cylinders of conductive spacer fabric. Details of such a sensor, including the manufacturing process, have been disclosed in U.S. patent application Ser. No. 13/333,600, entitled "Dry Gel-Conductive Scaffold Sensor," filed Dec. 21, 2011, and published as U.S. Patent Pub. No. 2012/0161783 on Jun. 28, 2012, which is hereby incorporated herein by reference. Advantageously, the disclosed unconventional electrodes are soft, yet mechanically robust. In addition, the hydrogel does not leave any traces on the skin, while still enabling low skin-electrode impedance (e.g., less than thirty kilo-ohms). In tests, the hybrid sensors were able to consistently provide an EEG signal that had a quality that was comparable to the quality of signals acquired with standard silver or silver-chloride (Ag/AgCl) electrodes in both time and frequency domains. The traces between the hybrid sensors and conventional sensors were nearly identical, which was confirmed by high values of the Pearson's coefficient and spectral coherence between the signals, and alpha rhythms were easily detected in the EEG signal acquired by the novel hybrid sensors. Furthermore, the hybrid sensors retained low impedances and excellent noise characteristics over a period as long as two months, if they are periodically rehydrated by soaking them in a thin layer of saline (e.g., 0.9% sodium-chloride (NaCl) solution) or water.

Notably, standard sleep staging techniques require multi-channel recordings of the scalp (i.e., EEG, EOG, and chin EMG), instead of forehead derivations of EEG. Thus, embodiments of the sleep mask, which utilize only forehead EEG signals, may relay the signals to a device (e.g., device 600), which provides innovative and unique algorithms for automated analysis of the frontopolar EEG signal to determine a subject's stage (depth) of sleep in real time. Specifically, device 600 may be configured or programmed to perform the EEG-based sleep staging disclosed in U.S. patent application Ser. No. 12/726,084, entitled "System for the Assessment of Sleep Quality in Adults and Children," filed Mar. 17, 2010, and published as U.S. Patent Pub. No. 2010/0240982 on Sep. 23, 2010, which is hereby incorporated herein by reference. Device 600 may store scores assigned to each thirty-second epoch of sleep into an internal flash memory, and may comprise a USB connector for data transfer and battery charging, and support wireless communication via a Bluetooth™ module.

Device 600 can be configured to either: (1) acquire two channels of electroencephalographic data from the forehead against a passive reference electrode (i.e., $F_{p1}$-$F_{pz}$ and $F_{p2}$-$F_{pz}$, as referenced in the 10-20 International System, described in the American Academy of Sleep Medicine (AASM) manual for the scoring of sleep and associated events, by Iber et al., and "EEG arousals: scoring rules and examples," by The Sleep Disorders Task Force of the American Sleep Disorders Association, both of which are hereby incorporated herein by reference); or (2) acquire a single EEG channel (i.e., $F_{p1}$-$F_{p2}$) while the $F_{pz}$ electrode serves as an active reference connected to the right-leg-drive (RLD) circuitry that feeds the common mode signals back to the subject, thereby providing an additional 20 decibels of the common mode signal suppression. By default, device 600 may be used in the two-channel configuration. However, the one-channel configuration may be beneficial in noisy environments, since most common unwanted signals in the EEG are all common-mode (e.g., power hum, electromagnetic interference).

In an embodiment, device 600 is a small, light-weight device with the specifications laid out below:

| Feature | Specifications |
| --- | --- |
| Size and weight | approx. 3.5 in. × 2.5 in. × 0.6 in.; and 3.5 oz. |
| Battery | rechargeable Lithium-polymer; 3.7 V; and 1,000 mAh. |
| Connectors | micro-USB for data transfer and charging |
| Input signals | Two EEG channels: bandwidth: 0.16-70 Hz; resolution: 0.5 µV/LSB; common-mode rejection ratio: >85 dB; and analog-to-digital converter: 12 bits, 256 S/s per channel. Three-axis accelerometer: analog-to-digital converter: 12 bits, 10 S/s per channel. |
| Sensory stimulation | Thermal: 102° F. max (1 A max current); selectable intensity (PWM); and selectable ON/OFF times. Visual: fixed brightness (5 ft-lm); and selectable patterns and ON/OFF times. Auditory: white noise only; and selectable intensity. |
| User interface | four multifunctional switches; 128 × 128 pixel RGB display; and graphical user interface (GUI) with menus. |
| Processor | Texas Instruments ™ MSP430F5529 microcontroller, 12 MHz clock; 256 kB flash memory; and pre-loaded with sleep staging algorithms. |
| USB | USB 2.0, 3 Mbps. |
| Bluetooth ™ | Class 2, v2 1 + EDR, 3 Mbps, 30 ft. (as pluggable USB module). |

Various embodiments of the disclosed systems and methods may be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A system for tailoring sleep architecture, the system comprising:
    one or more coupling elements configured to electrically couple a device to a mask;
    the mask, wherein the mask is configured to be worn by a user, and wherein the mask comprises
        one or more electroencephalographic sensors, wherein each of the one or more electroencephalographic sensors comprises hydrogel in a conductive spacer fabric,
        a heater element configured to generate heat, wherein the heater element comprises insulated first conductive thread electrically coupled to one or more of the one or more coupling elements,
        a visual element configured to generate light, wherein the visual element comprises one or more electroluminescent panels, and second conductive thread electrically coupled to one or more of the one or more coupling elements; and
    the device, wherein the device comprises a controller comprising one or more modules that, when the device is electrically coupled to the mask,
        receive one or more electroencephalographic signals from the one or more electroencephalographic sensors,
        determine a current sleep state and a target sleep state based, at least in part, on the one or more electroencephalographic signals, and,
        if the current sleep state and the target sleep state are different, control the heater element and the one or more electroluminescent panels, via the one or more coupling elements, to guide the user to the target sleep state.

2. The system of claim 1, wherein each of the first and second conductive threads comprises silver-coated conductive thread.

3. The system of claim 1, wherein the mask comprises one or more textile layers, and wherein each of the first and second conductive threads is embroidered into one or more of the one or more textile layers.

4. The system of claim 3, wherein the mask further comprises an insulating foam layer and an external cover.

5. The system of claim 1, wherein the mask is configured such that, when the mask is worn by a user, the one or more electroencephalographic sensors are positioned on the user's forehead and the one or more electroluminescent panels are positioned over the user's eyes.

6. The system of claim 1, wherein the one or more electroencephalographic sensors are configured to acquire two channels of electroencephalographic data from the user's forehead against a passive reference electrode.

7. The system of claim 1, wherein the one or more electroencephalographic sensors are configured to acquire one channel of electroencephalographic data from the user's forehead and utilize at least one electrode as an active reference.

8. The system of claim 1, wherein the one or more coupling elements comprise a first set of coupling elements and a second set of coupling elements which are configured to releasably connect to the first set of coupling elements, wherein the mask comprises the first set of coupling elements, wherein the device comprises a back side and a front side, and wherein the back side of the device comprises the second set of coupling elements and the front side of the device comprises a display, such that, when the second set of coupling elements of the device is releasably connected to the first set of coupling elements of the mask, the display is visible.

9. The system of claim 8, wherein the one or more modules are configured to display data related to a sleep architecture on the display.

10. The system of claim 1, wherein the mask further comprises an audio element configured to generate sound, wherein the audio element comprises one or more speakers, and third conductive thread electrically coupled to one or more of the one or more coupling elements.

11. The system of claim 10, wherein, when the device is electrically coupled to the mask, the one or more modules of the controller further control the audio element, via the one or more coupling elements, to guide the user to the target sleep state.

12. The system of claim 10, wherein the mask is configured such that, when the mask is worn by a user, the one or more speakers are positioned over the user's ears.

13. A system for tailoring sleep architecture, the system comprising:
    a mask configured to be worn by a user, wherein the mask comprises
        one or more electroencephalographic sensors, wherein each of the one or more electroencephalographic sensors is configured to acquire electrical activity from the user and output one or more electroencephalographic signals based on the acquired electrical activity, and
        a plurality of stimulation elements, wherein each of the plurality of stimulation elements is configured to provide one or more sensory stimuli to the user, and wherein the plurality of stimulation elements comprise a heater element and one or more electroluminescent panels; and
    a device comprising a controller comprising one or more modules that are configured to, when the device is electrically coupled to the mask,
        receive the one or more electroencephalographic signals from the one or more electroencephalographic sensors,
        determine a current sleep state and a target sleep state based, at least in part, on the one or more electroencephalographic signals, and,
        if the current sleep state and the target sleep state are different, control the heater element and the one or more electroluminescent panels to guide the user to the target sleep state.

14. The system of claim 13, wherein the system further comprises one or more conductive attachment elements that electrically couple the device to the mask.

15. The system of claim 14, wherein the one or more conductive attachment elements comprise a first set of attachment elements and a second set of attachment elements which correspond to the first set of attachment elements, wherein the mask comprises the first set of attachment elements and the device comprises the second set of attachment elements, and wherein the mask and the device are configured to be electrically coupled when the first set of attachment elements are coupled with the second set of attachment elements.

16. The system of claim 15, wherein the first set of attachment elements comprise one or more conductive snap halves and wherein the second set of attachment elements comprise one or more corresponding conductive snap halves.

17. The system of claim 14, wherein the mask further comprises a sensor layer comprising one or more electroencephalographic sensor sites and conductive thread which electrically couples the one or more electroencephalographic sensor sites to one or more of the one or more conductive attachment elements.

18. The system of claim 17, wherein each of the one or more electroencephalographic sensor sites comprises a hybrid electroencephalographic sensor comprising hydrogel in conductive spacer fabric.

19. The system of claim 14, wherein the heater element comprises a heating layer comprising insulated conductive thread which is electrically coupled to one or more of the one or more conductive attachment elements, wherein the insulated conductive thread is configured to emanate heat.

20. The system of claim 19, wherein the insulated conductive thread comprises silver-coated conductive thread insulated in plastic.

21. The system of claim 14, wherein the mask further comprises an audio layer comprising one or more speakers and conductive thread which electrically couples the one or more speakers to one or more of the one or more conductive attachment elements.

22. The system of claim 14, wherein the mask further comprises a visual layer comprising the one or more electroluminescent panels and conductive thread which electrically couples the one or more electroluminescent panels to one or more of the one or more conductive attachment elements.

23. The system of claim 13, wherein the device comprises a display, and wherein the one or more modules are configured to display data related to a sleep architecture of the user on the display.

* * * * *